US008168863B2

(12) United States Patent
Miles

(10) Patent No.: US 8,168,863 B2
(45) Date of Patent: May 1, 2012

(54) METHODS FOR ACCUMULATING HETEROLOGOUS POLYPEPTIDES IN PLANT STOVER UTILIZING A VACUOLE SORTING SIGNAL

(75) Inventor: Stacy Miles, Chapel Hill, NC (US)

(73) Assignee: Syngenta Participations AG, Basel (CH)

( * ) Notice: Subject to any disclaimer, the term of this patent is extended or adjusted under 35 U.S.C. 154(b) by 416 days.

(21) Appl. No.: 12/359,421

(22) Filed: Jan. 26, 2009

(65) Prior Publication Data

US 2009/0193541 A1 Jul. 30, 2009

Related U.S. Application Data

(60) Provisional application No. 61/024,844, filed on Jan. 30, 2008, provisional application No. 61/047,692, filed on Apr. 24, 2008.

(51) Int. Cl.
*C12N 15/82* (2006.01)
*C12N 5/14* (2006.01)
*A01H 5/00* (2006.01)
*C07H 21/04* (2006.01)

(52) U.S. Cl. ........ 800/288; 800/278; 800/287; 800/295; 800/298; 800/320.1; 536/23.1; 536/23.2; 536/23.4; 536/23.7; 536/23.74; 435/419

(58) Field of Classification Search .................. None
See application file for complete search history.

(56) References Cited

U.S. PATENT DOCUMENTS

| | | | |
|---|---|---|---|
| 5,168,064 | A | 12/1992 | Bennett et al. |
| 5,981,835 | A | 11/1999 | Austin-Phillips et al. |
| 6,013,860 | A | 1/2000 | Himmel et al. |
| 6,818,803 | B1 | 11/2004 | Austin-Phillips et al. |
| 7,049,485 | B2 | 5/2006 | Sticklen et al. |
| 2002/0138878 | A1 | 9/2002 | Sticklen et al. |
| 2003/0109011 | A1 | 6/2003 | Hood et al. |
| 2003/0135885 | A1 | 7/2003 | Lanahan et al. |
| 2003/0145346 | A1 | 7/2003 | Hood et al. |
| 2005/0172356 | A1 | 8/2005 | Christeller |
| 2006/0026715 | A1* | 2/2006 | Hood et al. ................ 800/284 |
| 2007/0192900 | A1 | 8/2007 | Sticklen |
| 2007/0226840 | A1 | 9/2007 | Bae et al. |
| 2007/0250961 | A1 | 10/2007 | Blaylock et al. |
| 2008/0118954 | A1 | 5/2008 | Sticklen |
| 2008/0289066 | A1 | 11/2008 | Lanahan et al. |

FOREIGN PATENT DOCUMENTS

| | | |
|---|---|---|
| WO | 91/16440 | 10/1991 |
| WO | 92/01042 | 1/1992 |
| WO | 98/11235 | 3/1998 |
| WO | 00/05381 | 2/2000 |
| WO | 2006/101584 | 9/2006 |

OTHER PUBLICATIONS

Cervelli et al. A novel C-terminal sequence from barley polyamine oxidase is a vacuolar sorting signal. (2004) The Plant Journal; vol. 40; pp. 410-418.*

Database Uniprot [Online], Aug. 1, 1988, "cbh2 Trichoderma reesei (Hypocrea jecorina)", XP002518726, EBI Database Accession No. P07987.
Database Geneseq [Online], Dec. 15, 2005, "Cellobiohydrolase II Hypocrea Jecorina", XP002518728, EBI Database Accession No. AED46540.
Database Uniprot [Online], Oct. 11, 2004, "cbh1 Penicillium occitanis", XP002518727, EBI Database Accession No. Q68HC2.
Database Uniprot [Online], Jul. 19, 2004, "cbh2 Trichoderma harzianum (Hypocrea Iixii)", XP002518729, EBI Database Accession No. Q9P8P3.
Alessandro Vitale & Natasha V. Raikhel, "What do Proteins Need to Reach Different Vacuoles?", Trends in Science, vol. 4, No. 4, Apr. 1999, pp. 149-155, XP002518725.
Syngenta Participations AG, PCT/ISA/206 Communication Relating to the Results of the Partial International Search Report, May 18, 2009, pp. 1-2.
Cervelli et al., "A novel C-terminal sequence from barley polyamine oxidase is a vacuolar sorting signal", Plant Journal, vol. 40, (2004) pp. 410-418.
Montalvo-Rodriguez, "Autohydrolysis of Plant Polysaccharides Using Transgenic Hyperthermophilic Enzymes", Biotechnology and Bioengineering, vol. 70, No. 2 (Oct. 20, 2000) pp. 151-159.
Ziegelhoffer et al., "Dramatic effects of truncation and sub-cellular targeting on the accumulation of recombinant microbial cellulase in tobacco", Molecular Breeding, vol. 8 (2001) pp. 147-158.
Lashbrook et al., Functional Analysis of Cx-Cellulase (Endoβ-1-4-Glucanase) Gene Expression in Transgenic Tomato Fruit, Cellular and Molecular Aspects of the Plant Hormone Ethylene, J.C. Pech et al. (eds) (Kluwer Academic Publishers), (1993). pp. 123-128.
Koehler et al., "The Gene Promoter for a bean Abscission Cellulase is Ethylene-Induced in Transgenic Tomato and Shows High Sequence Conservation with a Soybean Abscission Cellulase", Plant Molecular Biology, vol. 31, pp. 595-606, (1996).
Melchers et al., Extracellular Targeting of the Vacuolar Tobacco Proteins AP24, Chitinase and B-1, 3-glucanase in Transgenic Plants, 1993, Plant Molecular Biology, vol. 21, pp. 583-593.
Neuhaus and Rogers. "Sorting of Proteins to Vacuoles in Plant Cells" *Plant Molecular Biology* 38:127-144 (1998).
Robinson et al. "Protein Sorting to the Storage Vacuoles of Plants: A Critical Appraisal" *Traffic* 6:615-625 (2005).

* cited by examiner

*Primary Examiner* — Cathy Kingdon Worley
(74) *Attorney, Agent, or Firm* — Joshua L. Price

(57) ABSTRACT

Compositions and methods for increasing the expression and/or accumulation of cellobiohydrolase enzyme in the vacuoles of plant cells are provided. The method involves targeting the enzyme to the vacuoles through the use of a barley polyamine oxidase (BPAO) vacuole sorting signal peptide. Plants transformed with an expression construct encoding the vacuole sorting signal peptide operably linked to the cellobiohydrolase enzyme direct expression of the polypeptide to the vacuoles of the plant cells. Transgenic plants, seeds, and plant tissues, and plant parts are provided. Downstream uses of transgenic plants or plant material expressing the constructs of the invention include agronomical and industrial uses, for example, human food, animal feed, biofuel, industrial alcohol, fermentation feedstocks, and the like.

26 Claims, No Drawings

SEQUENCE LISTING

<160> NUMBER OF SEQ ID NOS: 21

<210> SEQ ID NO 1
<211> LENGTH: 24
<212> TYPE: DNA
<213> ORGANISM: Hordeum vulgare
<220> FEATURE:
<221> NAME/KEY: CDS
<222> LOCATION: (1)...(24)

<400> SEQUENCE: 1 gac gag ctg aaa gct gag gct aaa                        24

-continued

Asp Glu Leu Lys Ala Glu Ala Lys
1               5

<210> SEQ ID NO 2
<211> LENGTH: 8
<212> TYPE: PRT
<213> ORGANISM: Hordeum vulgare

<400> SEQUENCE: 2

Asp Glu Leu Lys Ala Glu Ala Lys
1               5

<210> SEQ ID NO 3
<211> LENGTH: 19
<212> TYPE: PRT
<213> ORGANISM: Glycine max

<400> SEQUENCE: 3

Met Ala Lys Leu Val Phe Ser Leu Cys Phe Leu Leu Phe Ser Gly Cys
1               5                   10                  15

Cys Phe Ala

<210> SEQ ID NO 4
<211> LENGTH: 6
<212> TYPE: PRT
<213> ORGANISM: Artificial Sequence
<220> FEATURE:
<223> OTHER INFORMATION: Endoplasmic reticulum signal sequence

<400> SEQUENCE: 4

Ser Glu Lys Asp Glu Leu
1               5

<210> SEQ ID NO 5
<211> LENGTH: 11
<212> TYPE: PRT
<213> ORGANISM: Ipomoea batatas

<400> SEQUENCE: 5

Arg Phe Asn Pro Ile Arg Leu Pro Thr Thr His
1               5                   10

<210> SEQ ID NO 6
<211> LENGTH: 66
<212> TYPE: PRT
<213> ORGANISM: Cyanophora paradoxa

<400> SEQUENCE: 6

Met Ala Phe Val Ala Ser Val Pro Val Phe Ala Asn Ala Ser Gly Leu
1               5                   10                  15

Lys Thr Glu Ala Lys Val Cys Gln Lys Pro Ala Leu Lys Asn Ser Phe
            20                  25                  30

Phe Arg Gly Glu Glu Val Thr Ser Arg Ser Phe Phe Ala Ser Gln
        35                  40                  45

Ala Val Ser Ala Lys Pro Ala Thr Thr Gly Glu Val Asp Thr Thr Ile
    50                  55                  60

Arg Ala
65

<210> SEQ ID NO 7
<211> LENGTH: 10
<212> TYPE: PRT
<213> ORGANISM: Glycine max

```
-continued

<400> SEQUENCE: 7

Pro Leu Ser Ser Ile Leu Arg Ala Phe Tyr
1               5                   10

<210> SEQ ID NO 8
<211> LENGTH: 19
<212> TYPE: PRT
<213> ORGANISM: Zea mays

<400> SEQUENCE: 8

Met Arg Val Leu Leu Val Ala Leu Ala Leu Leu Ala Leu Ala Ala Ser
1               5                   10                  15

Ala Thr Ser

<210> SEQ ID NO 9
<211> LENGTH: 654
<212> TYPE: DNA
<213> ORGANISM: Cestrum yellow leaf curling virus

<400> SEQUENCE: 9
gtttaattac tggcagacaa agtggcagac atactgtccc acaaatgaag atggaatctg      60
taaaagaaaa cgcgtgaaat aatgcgtctg acaaaggtta ggtcggctgc ctttaatcaa     120
taccaaagtg gtccctacca cgatggaaaa actgtgcagt cggtttggct ttttctgacg     180
aacaaataag attcgtggcc gacaggtggg ggtccaccat gtgaaggcat cttcagactc     240
caataatgga gcaatgacgt aagggcttac gaaataagta agggtagttt gggaaatgtc     300
cactcacccg tcagtctata atacttagc ccctccctca ttgttaaggg agcaaaatct      360
cagagagata gtcctagaga gagaaagaga gcaagtagcc tagaagtagt caaggcggcg     420
aagtattcag gcaggtggcc aggaagaaga aaagccaaga cgacgaaaac aggtaagagc     480
taagctttct catctcaaag atgattcttg atgattttg tctccaccgt ccgtatagga      540
tcactgaatt gataaatatc atatggtttg tataaaaccc gatatttaaa tctgtatcat     600
tctgtttgaa taaaacttga tactttgttg gagtcgtttg taaaaacata aacc           654

<210> SEQ ID NO 10
<211> LENGTH: 1518
<212> TYPE: DNA
<213> ORGANISM: Artificial Sequence
<220> FEATURE:
<223> OTHER INFORMATION: synthetic sequence encoding cellulobiohydrolase
      I
<221> NAME/KEY: CDS
<222> LOCATION: (1)...(1518)

<400> SEQUENCE: 10 atg caa cag att gga act tac acc gct gag acc cat cca tct ttg tct       48
Met Gln Gln Ile Gly Thr Tyr Thr Ala Glu Thr His Pro Ser Leu Ser
1               5                   10                  15 tgg tct acc tgc aag tct ggt gga tct tgc act act aac tcc ggt gct       96
Trp Ser Thr Cys Lys Ser Gly Gly Ser Cys Thr Thr Asn Ser Gly Ala
            20                  25                  30 att acc ctt gat gcc aat tgg aga tgg gtt cac ggt gtt aac act tcc      144
Ile Thr Leu Asp Ala Asn Trp Arg Trp Val His Gly Val Asn Thr Ser
        35                  40                  45 act aac tgc tac act gga aac act tgg aac acc gct att tgc gat act      192
Thr Asn Cys Tyr Thr Gly Asn Thr Trp Asn Thr Ala Ile Cys Asp Thr
    50                  55                  60 gat gct tct tgc gct caa gat tgc gct ctt gat ggt gct gat tac tct      240
Asp Ala Ser Cys Ala Gln Asp Cys Ala Leu Asp Gly Ala Asp Tyr Ser
65                  70                  75                  80
```

| | | |
|---|---|---|
| gga acc tac gga att acc acc tct gga aac tcc ctt agg ctt aac ttc<br>Gly Thr Tyr Gly Ile Thr Thr Ser Gly Asn Ser Leu Arg Leu Asn Phe<br>                    85                          90                    95 | 288 |
| gtg acc gga tct aat gtt gga tct agg acc tac ctc atg gct gat aac<br>Val Thr Gly Ser Asn Val Gly Ser Arg Thr Tyr Leu Met Ala Asp Asn<br>                   100                          105                    110 | 336 |
| acc cac tac cag atc ttc gat ctc ctc aac cag gag ttc act ttc acc<br>Thr His Tyr Gln Ile Phe Asp Leu Leu Asn Gln Glu Phe Thr Phe Thr<br>            115                          120                      125 | 384 |
| gtt gat gtg tct cat ctt cca tgc gga ctt aac ggt gct ctt tac ttc<br>Val Asp Val Ser His Leu Pro Cys Gly Leu Asn Gly Ala Leu Tyr Phe<br>130                       135                          140 | 432 |
| gtg act atg gat gct gat ggt gga gtt tcc aag tac cca aac aac aag<br>Val Thr Met Asp Ala Asp Gly Gly Val Ser Lys Tyr Pro Asn Asn Lys<br>145                     150                       155                 160 | 480 |
| gct ggt gct caa tat ggt gtt gga tac tgc gat tct caa tgc cca agg<br>Ala Gly Ala Gln Tyr Gly Val Gly Tyr Cys Asp Ser Gln Cys Pro Arg<br>                   165                          170                    175 | 528 |
| gac ctc aag ttc att gct gga cag gct aac gtt gaa gga tgg acc cca<br>Asp Leu Lys Phe Ile Ala Gly Gln Ala Asn Val Glu Gly Trp Thr Pro<br>             180                          185                      190 | 576 |
| tct tct aac aac gct aac acc gga ctt gga aat cat ggt gct tgc tgc<br>Ser Ser Asn Asn Ala Asn Thr Gly Leu Gly Asn His Gly Ala Cys Cys<br>                   195                          200                    205 | 624 |
| gct gaa ctt gat att tgg gag gcc aac tct att tct gag gct ctt acc<br>Ala Glu Leu Asp Ile Trp Glu Ala Asn Ser Ile Ser Glu Ala Leu Thr<br>210                     215                       220 | 672 |
| cca cat cca tgc gat act cca gga ctt tct gtg tgc act act gat gct<br>Pro His Pro Cys Asp Thr Pro Gly Leu Ser Val Cys Thr Thr Asp Ala<br>225                     230                       235                 240 | 720 |
| tgc gga gga acc tat tct tcc gat aga tac gct gga act tgc gat cca<br>Cys Gly Gly Thr Tyr Ser Ser Asp Arg Tyr Ala Gly Thr Cys Asp Pro<br>                   245                          250                    255 | 768 |
| gat gga tgc gat ttc aac cca tac agg ctt gga gtt acc gat ttc tac<br>Asp Gly Cys Asp Phe Asn Pro Tyr Arg Leu Gly Val Thr Asp Phe Tyr<br>             260                          265                      270 | 816 |
| ggt tct gga aag act gtt gac acc acc aag cca att act gtt gtg acc<br>Gly Ser Gly Lys Thr Val Asp Thr Thr Lys Pro Ile Thr Val Val Thr<br>                   275                          280                    285 | 864 |
| cag ttc gtt act gat gat gga act tcc acc gga acc ctt tct gag atc<br>Gln Phe Val Thr Asp Asp Gly Thr Ser Thr Gly Thr Leu Ser Glu Ile<br>             290                          295                      300 | 912 |
| aga agg tac tac gtt cag aac ggt gtt gtt att cca cag cca tcc tcc<br>Arg Arg Tyr Tyr Val Gln Asn Gly Val Val Ile Pro Gln Pro Ser Ser<br>305                     310                       315                 320 | 960 |
| aag att tct ggt gtg tcc gga aac gtg att aac tcc gat ttc tgc gat<br>Lys Ile Ser Gly Val Ser Gly Asn Val Ile Asn Ser Asp Phe Cys Asp<br>                   325                          330                    335 | 1008 |
| gct gag att tct act ttc gga gag acc gct tct ttt tct aag cac ggc<br>Ala Glu Ile Ser Thr Phe Gly Glu Thr Ala Ser Phe Ser Lys His Gly<br>             340                          345                    350 | 1056 |
| gga ctt gct aaa atg gga gct gga atg gaa gca gga atg gtg ctt gtg<br>Gly Leu Ala Lys Met Gly Ala Gly Met Glu Ala Gly Met Val Leu Val<br>                   355                          360                    365 | 1104 |
| atg tcc ctt tgg gat gat tac tcc gtg aac atg ctt tgg ctt gat tct<br>Met Ser Leu Trp Asp Asp Tyr Ser Val Asn Met Leu Trp Leu Asp Ser<br>             370                          375                    380 | 1152 |
| acc tac cca act aac gct act gga act cca ggt gct gct aga gga tct<br>Thr Tyr Pro Thr Asn Ala Thr Gly Thr Pro Gly Ala Ala Arg Gly Ser<br>385                     390                       395                 400 | 1200 |

```
tgc cca act act tcc ggt gat cca aag acc gtt gag tct cag tct gga    1248
Cys Pro Thr Thr Ser Gly Asp Pro Lys Thr Val Glu Ser Gln Ser Gly
            405                 410                 415 tct tct tac gtg acc ttc tcc gat att aga gtg gga cca ttc aac tct    1296
Ser Ser Tyr Val Thr Phe Ser Asp Ile Arg Val Gly Pro Phe Asn Ser
            420                 425                 430 act ttc tcc ggt gga tct tct act ggt ggt tct tct act act acc gct    1344
Thr Phe Ser Gly Gly Ser Ser Thr Gly Gly Ser Ser Thr Thr Thr Ala
            435                 440                 445 tct gga act act act acc aag gct tct tct acc tct acc tct tct act    1392
Ser Gly Thr Thr Thr Thr Lys Ala Ser Ser Thr Ser Thr Ser Ser Thr
450                 455                 460 tct act gga acc ggt gtt gct gct cat tgg gga caa tgt gga gga caa    1440
Ser Thr Gly Thr Gly Val Ala Ala His Trp Gly Gln Cys Gly Gly Gln
465                 470                 475                 480 gga tgg act gga cca act act tgc gct tca gga act acc tgc acc gtt    1488
Gly Trp Thr Gly Pro Thr Thr Cys Ala Ser Gly Thr Thr Cys Thr Val
            485                 490                 495 gtg aac cct tac tac tct cag tgc ctt tga                            1518
Val Asn Pro Tyr Tyr Ser Gln Cys Leu *
            500                 505

<210> SEQ ID NO 11
<211> LENGTH: 505
<212> TYPE: PRT
<213> ORGANISM: Artificial Sequence
<220> FEATURE:
<223> OTHER INFORMATION: cellubiohydrolase I sequence encoded by
      synthetic gene

<400> SEQUENCE: 11

Met Gln Gln Ile Gly Thr Tyr Thr Ala Glu Thr His Pro Ser Leu Ser
 1               5                  10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
 50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
    130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
```

```
                210                 215                 220
Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Thr Lys Pro Ile Thr Val Val Thr
        275                 280                 285

Gln Phe Val Thr Asp Asp Gly Thr Ser Thr Gly Thr Leu Ser Glu Ile
290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Gly Thr Ala Ser Phe Ser Lys His Gly
            340                 345                 350

Gly Leu Ala Lys Met Gly Ala Gly Met Glu Ala Gly Met Val Leu Val
        355                 360                 365

Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
            420                 425                 430

Thr Phe Ser Gly Gly Ser Ser Thr Gly Gly Ser Ser Thr Thr Thr Ala
        435                 440                 445

Ser Gly Thr Thr Thr Lys Ala Ser Ser Thr Ser Thr Ser Ser Ser Thr
450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
            500                 505

<210> SEQ ID NO 12
<211> LENGTH: 1368
<212> TYPE: DNA
<213> ORGANISM: Artificial Sequence
<220> FEATURE:
<223> OTHER INFORMATION: synthetic sequence encoding cellulobiohydrolase
      2
<221> NAME/KEY: CDS
<222> LOCATION: (1)...(1368)

<400> SEQUENCE: 12 atg gtt cca ctt gag gaa agg cag tct tgc tct tct gtt tgg gga caa    48
Met Val Pro Leu Glu Glu Arg Gln Ser Cys Ser Ser Val Trp Gly Gln
1               5                   10                  15 tgc gga gga caa aat tgg gct gga cca ttc tgt tgt gct tca gga tct    96
Cys Gly Gly Gln Asn Trp Ala Gly Pro Phe Cys Cys Ala Ser Gly Ser
            20                  25                  30 acc tgc gtg tac tcc aac gat tac tac tct cag tgc ctt cca gga act   144
Thr Cys Val Tyr Ser Asn Asp Tyr Tyr Ser Gln Cys Leu Pro Gly Thr
        35                  40                  45
```

```
gct tct tct tct tcc tct acc agg gct tct tct act acc tct agg gtg        192
Ala Ser Ser Ser Ser Ser Thr Arg Ala Ser Ser Thr Thr Ser Arg Val
 50              55                  60 tca tct gct act tct acc agg tct agc tct tct act cca cca cct gct        240
Ser Ser Ala Thr Ser Thr Arg Ser Ser Ser Ser Thr Pro Pro Pro Ala
 65              70                  75                  80 tca tct act act cca gct cca cca gtt gga tct gga act gct acc tac        288
Ser Ser Thr Thr Pro Ala Pro Pro Val Gly Ser Gly Thr Ala Thr Tyr
                 85                  90                  95 tct gga aac cca ttc gct ggt gtt aca cct tgg gct aac tca ttc tac        336
Ser Gly Asn Pro Phe Ala Gly Val Thr Pro Trp Ala Asn Ser Phe Tyr
            100                 105                 110 gct tca gag gtg tca act ctc gct att cca tct ctt act ggc gct atg        384
Ala Ser Glu Val Ser Thr Leu Ala Ile Pro Ser Leu Thr Gly Ala Met
        115                 120                 125 gct act gct gct gct gcc gtt gct aag gtt cca tct ttc atg tgg ctc        432
Ala Thr Ala Ala Ala Ala Val Ala Lys Val Pro Ser Phe Met Trp Leu
130                 135                 140 gat acc ctt gat aag acc cca ctt atg tcc tct acc ctc tcc gat att        480
Asp Thr Leu Asp Lys Thr Pro Leu Met Ser Ser Thr Leu Ser Asp Ile
145                 150                 155                 160 agg gct gct aac aag gca ggt gga aac tat gct gga cag ttc gtg gtt        528
Arg Ala Ala Asn Lys Ala Gly Gly Asn Tyr Ala Gly Gln Phe Val Val
                165                 170                 175 tac gat ctc cca gat aga gat tgc gct gct gct gct tct aac ggt gag        576
Tyr Asp Leu Pro Asp Arg Asp Cys Ala Ala Ala Ala Ser Asn Gly Glu
            180                 185                 190 tac tcc att gct gat ggt gga gtg gct aag tac aag aac tac atc gat        624
Tyr Ser Ile Ala Asp Gly Gly Val Ala Lys Tyr Lys Asn Tyr Ile Asp
        195                 200                 205 acc att agg ggt att gtg acc acc ttc tcc gat gtg agg att ctt ctc        672
Thr Ile Arg Gly Ile Val Thr Thr Phe Ser Asp Val Arg Ile Leu Leu
210                 215                 220 gtg att gag cca gat tct ctt gct aac ctc gtg act aac ctt gct act        720
Val Ile Glu Pro Asp Ser Leu Ala Asn Leu Val Thr Asn Leu Ala Thr
225                 230                 235                 240 cca aag tgc tct aac gct cag tct gct tac ctt gag tgc atc aac tac        768
Pro Lys Cys Ser Asn Ala Gln Ser Ala Tyr Leu Glu Cys Ile Asn Tyr
                245                 250                 255 gct att acc cag ctt aac ctc cca aac gtg gct atg tat ctc gat gct        816
Ala Ile Thr Gln Leu Asn Leu Pro Asn Val Ala Met Tyr Leu Asp Ala
            260                 265                 270 gga cat gct gga tgg ctt gga tgg cca gct aat cag gac cca gct gct        864
Gly His Ala Gly Trp Leu Gly Trp Pro Ala Asn Gln Asp Pro Ala Ala
        275                 280                 285 caa ctt ttc gcc aac gtg tac aag aac gct tct tct cca aga gct gtt        912
Gln Leu Phe Ala Asn Val Tyr Lys Asn Ala Ser Ser Pro Arg Ala Val
290                 295                 300 agg gga ctt gct acc aac gtt gct aac tac aac gct tgg aac att act        960
Arg Gly Leu Ala Thr Asn Val Ala Asn Tyr Asn Ala Trp Asn Ile Thr
305                 310                 315                 320 acc cca cca tct tac act cag gga aac gct gtt tac aac gag aag ctc       1008
Thr Pro Pro Ser Tyr Thr Gln Gly Asn Ala Val Tyr Asn Glu Lys Leu
                325                 330                 335 tac att cat gct ctt gga cca ctt ttg gct aac cac gga tgg tct aac       1056
Tyr Ile His Ala Leu Gly Pro Leu Leu Ala Asn His Gly Trp Ser Asn
            340                 345                 350 gct ttc ttc atc acc gat cag gga aga tct gga aag caa cct act gga       1104
Ala Phe Phe Ile Thr Asp Gln Gly Arg Ser Gly Lys Gln Pro Thr Gly
        355                 360                 365
```

```
caa ctt gag tgg gga aac tgg tgt aac gct gtt gga acc gga ttc gga    1152
Gln Leu Glu Trp Gly Asn Trp Cys Asn Ala Val Gly Thr Gly Phe Gly
    370                 375                 380 att agg cca tct gct aac acc ggt gat tct ctc ctc gat tcc ttt gtg    1200
Ile Arg Pro Ser Ala Asn Thr Gly Asp Ser Leu Leu Asp Ser Phe Val
385                 390                 395                 400 tgg att aag cca ggt gga gag tgc gat gga acc tct aac tct tct gcc    1248
Trp Ile Lys Pro Gly Gly Glu Cys Asp Gly Thr Ser Asn Ser Ser Ala
            405                 410                 415 cca aga ttc gat tac cat tgc gct tca gct gat gct ctt caa cca gct    1296
Pro Arg Phe Asp Tyr His Cys Ala Ser Ala Asp Ala Leu Gln Pro Ala
        420                 425                 430 cca caa gct ggt tct tgg ttt cag gcc tac ttc gtt cag ctt ctc act    1344
Pro Gln Ala Gly Ser Trp Phe Gln Ala Tyr Phe Val Gln Leu Leu Thr
    435                 440                 445 aac gct aac cca tct ttc ctt tga                                    1368
Asn Ala Asn Pro Ser Phe Leu  *
450                 455
```

<210> SEQ ID NO 13
<211> LENGTH: 455
<212> TYPE: PRT
<213> ORGANISM: Artificial Sequence
<220> FEATURE:
<223> OTHER INFORMATION: cellulobiohydrolase 2 sequence encoded by
      synthetic gene

<400> SEQUENCE: 13

```
Met Val Pro Leu Glu Glu Arg Gln Ser Cys Ser Ser Val Trp Gly Gln
  1               5                  10                  15

Cys Gly Gly Gln Asn Trp Ala Gly Pro Phe Cys Cys Ala Ser Gly Ser
             20                  25                  30

Thr Cys Val Tyr Ser Asn Asp Tyr Tyr Ser Gln Cys Leu Pro Gly Thr
         35                  40                  45

Ala Ser Ser Ser Ser Thr Arg Ala Ser Ser Thr Thr Ser Arg Val
     50                  55                  60

Ser Ser Ala Thr Ser Thr Arg Ser Ser Ser Thr Pro Pro Ala
 65                  70                  75                  80

Ser Ser Thr Thr Pro Ala Pro Val Gly Ser Gly Thr Ala Thr Tyr
                 85                  90                  95

Ser Gly Asn Pro Phe Ala Gly Val Thr Pro Trp Ala Asn Ser Phe Tyr
            100                 105                 110

Ala Ser Glu Val Ser Thr Leu Ala Ile Pro Ser Leu Thr Gly Ala Met
        115                 120                 125

Ala Thr Ala Ala Ala Val Ala Lys Val Pro Ser Phe Met Trp Leu
    130                 135                 140

Asp Thr Leu Asp Lys Thr Pro Leu Met Ser Ser Thr Leu Ser Asp Ile
145                 150                 155                 160

Arg Ala Ala Asn Lys Ala Gly Gly Asn Tyr Ala Gly Gln Phe Val Val
                165                 170                 175

Tyr Asp Leu Pro Asp Arg Asp Cys Ala Ala Ala Ser Asn Gly Glu
            180                 185                 190

Tyr Ser Ile Ala Asp Gly Gly Val Ala Lys Tyr Lys Asn Tyr Ile Asp
        195                 200                 205

Thr Ile Arg Gly Ile Val Thr Thr Phe Ser Asp Val Arg Ile Leu Leu
    210                 215                 220

Val Ile Glu Pro Asp Ser Leu Ala Asn Leu Val Thr Asn Leu Ala Thr
225                 230                 235                 240
```

```
Pro Lys Cys Ser Asn Ala Gln Ser Ala Tyr Leu Glu Cys Ile Asn Tyr
            245                 250                 255

Ala Ile Thr Gln Leu Asn Leu Pro Asn Val Ala Met Tyr Leu Asp Ala
        260                 265                 270

Gly His Ala Gly Trp Leu Gly Trp Pro Ala Asn Gln Asp Pro Ala Ala
    275                 280                 285

Gln Leu Phe Ala Asn Val Tyr Lys Asn Ala Ser Ser Pro Arg Ala Val
290                 295                 300

Arg Gly Leu Ala Thr Asn Val Ala Asn Tyr Asn Ala Trp Asn Ile Thr
305                 310                 315                 320

Thr Pro Pro Ser Tyr Thr Gln Gly Asn Ala Val Tyr Asn Glu Lys Leu
                325                 330                 335

Tyr Ile His Ala Leu Gly Pro Leu Leu Ala Asn His Gly Trp Ser Asn
            340                 345                 350

Ala Phe Phe Ile Thr Asp Gln Gly Arg Ser Gly Lys Gln Pro Thr Gly
        355                 360                 365

Gln Leu Glu Trp Gly Asn Trp Cys Asn Ala Val Gly Thr Gly Phe Gly
    370                 375                 380

Ile Arg Pro Ser Ala Asn Thr Gly Asp Ser Leu Leu Asp Ser Phe Val
385                 390                 395                 400

Trp Ile Lys Pro Gly Gly Glu Cys Asp Gly Thr Ser Asn Ser Ser Ala
                405                 410                 415

Pro Arg Phe Asp Tyr His Cys Ala Ser Ala Asp Ala Leu Gln Pro Ala
            420                 425                 430

Pro Gln Ala Gly Ser Trp Phe Gln Ala Tyr Phe Val Gln Leu Leu Thr
        435                 440                 445

Asn Ala Asn Pro Ser Phe Leu
    450                 455

<210> SEQ ID NO 14
<211> LENGTH: 1518
<212> TYPE: DNA
<213> ORGANISM: Artificial Sequence
<220> FEATURE:
<223> OTHER INFORMATION: synthetic sequence encoding cellobiohydrolase I
<221> NAME/KEY: CDS
<222> LOCATION: (1)...(1518)

<400> SEQUENCE: 14 atg cag cag atc ggc acc tac acc gcc gag acc cac cca agc ctg agc      48
Met Gln Gln Ile Gly Thr Tyr Thr Ala Glu Thr His Pro Ser Leu Ser
1               5                   10                  15 tgg tcc acc tgc aag agc ggc ggt tcc tgc acg acc aac agc ggc gcc      96
Trp Ser Thr Cys Lys Ser Gly Gly Ser Cys Thr Thr Asn Ser Gly Ala
            20                  25                  30 atc acc ctt gat gcg aac tgg cgc tgg gtg cac ggc gtg aac acc agc     144
Ile Thr Leu Asp Ala Asn Trp Arg Trp Val His Gly Val Asn Thr Ser
        35                  40                  45 acc aac tgc tac acg ggt aac acg tgg aac acc gcc atc tgc gac acg     192
Thr Asn Cys Tyr Thr Gly Asn Thr Trp Asn Thr Ala Ile Cys Asp Thr
    50                  55                  60 gac gct tcc tgc gcc cag gac tgc gcg ctt gat ggc gcc gac tac tcc     240
Asp Ala Ser Cys Ala Gln Asp Cys Ala Leu Asp Gly Ala Asp Tyr Ser
65                  70                  75                  80 ggc acc tac ggc atc acc acc tcc ggc aac agc ctg cgc ctg aac ttc     288
Gly Thr Tyr Gly Ile Thr Thr Ser Gly Asn Ser Leu Arg Leu Asn Phe
                85                  90                  95 gtg acc ggc agc aat gtg ggc agc cgc acc tac ctg atg gcc gac aac     336
```

```
                    Val Thr Gly Ser Asn Val Gly Ser Arg Thr Tyr Leu Met Ala Asp Asn
                            100                 105                 110 acc cac tac cag atc ttc gac ctg ctg aac cag gag ttc acc ttc acc       384
Thr His Tyr Gln Ile Phe Asp Leu Leu Asn Gln Glu Phe Thr Phe Thr
            115                 120                 125 gtc gac gtg tcc cac ctg ccc tgc ggc ctg aac ggc gcc ctc tac ttc       432
Val Asp Val Ser His Leu Pro Cys Gly Leu Asn Gly Ala Leu Tyr Phe
130                 135                 140 gtg acg atg gac gcc gac ggc ggc gtg tcc aag tac ccg aac aac aag       480
Val Thr Met Asp Ala Asp Gly Gly Val Ser Lys Tyr Pro Asn Asn Lys
145                 150                 155                 160 gct ggc gcc cag tac ggt gtg ggc tac tgc gac agc cag tgc ccg agg       528
Ala Gly Ala Gln Tyr Gly Val Gly Tyr Cys Asp Ser Gln Cys Pro Arg
                165                 170                 175 gac ctg aag ttc atc gcc ggc cag gcc aac gtg gag ggc tgg acc ccg       576
Asp Leu Lys Phe Ile Ala Gly Gln Ala Asn Val Glu Gly Trp Thr Pro
            180                 185                 190 agc agc aac aac gcc aac acc ggc ctg ggc aac cac ggc gcc tgc tgc       624
Ser Ser Asn Asn Ala Asn Thr Gly Leu Gly Asn His Gly Ala Cys Cys
        195                 200                 205 gcc gag ctg gac atc tgg gag gcc aac agc atc agc gag gcc ctg acc       672
Ala Glu Leu Asp Ile Trp Glu Ala Asn Ser Ile Ser Glu Ala Leu Thr
    210                 215                 220 cca cac cca tgc gac acc cca ggc ctg tct gtg tgc acc acc gac gcc       720
Pro His Pro Cys Asp Thr Pro Gly Leu Ser Val Cys Thr Thr Asp Ala
225                 230                 235                 240 tgc ggc ggc acc tac tcc agc gac cgc tac gcc ggc acc tgc gac cca       768
Cys Gly Gly Thr Tyr Ser Ser Asp Arg Tyr Ala Gly Thr Cys Asp Pro
                245                 250                 255 gac ggc tgc gac ttc aac ccg tac cgc ctg ggc gtg acc gac ttc tac       816
Asp Gly Cys Asp Phe Asn Pro Tyr Arg Leu Gly Val Thr Asp Phe Tyr
            260                 265                 270 ggc agc ggc aag acc gtg gac acc acc aag ccg atc acc gtg gtg acc       864
Gly Ser Gly Lys Thr Val Asp Thr Thr Lys Pro Ile Thr Val Val Thr
        275                 280                 285 cag ttc gtg acc gac gac ggc acc agc acc ggc acc ctg agc gag atc       912
Gln Phe Val Thr Asp Asp Gly Thr Ser Thr Gly Thr Leu Ser Glu Ile
    290                 295                 300 cgc cgc tac tac gtc cag aac ggc gtg gtg atc ccg cag ccg agc agc       960
Arg Arg Tyr Tyr Val Gln Asn Gly Val Val Ile Pro Gln Pro Ser Ser
305                 310                 315                 320 aag atc agc ggc gtg tcc ggc aac gtg atc aac agc gac ttc tgc gac      1008
Lys Ile Ser Gly Val Ser Gly Asn Val Ile Asn Ser Asp Phe Cys Asp
                325                 330                 335 gcc gag atc agc acc ttc ggc gag acc gcc agc ttc agc aag cac ggc      1056
Ala Glu Ile Ser Thr Phe Gly Glu Thr Ala Ser Phe Ser Lys His Gly
            340                 345                 350 ggc ctg gcc aag atg ggc gct ggc atg gaa gcc ggc atg gtg ctg gtg      1104
Gly Leu Ala Lys Met Gly Ala Gly Met Glu Ala Gly Met Val Leu Val
        355                 360                 365 atg agc ctg tgg gac gac tac tcc gtg aac atg ctg tgg ctg gac agc      1152
Met Ser Leu Trp Asp Asp Tyr Ser Val Asn Met Leu Trp Leu Asp Ser
    370                 375                 380 acc tac ccg acc aac gcc acc ggg acg cca ggc gct gcc agg ggc agc      1200
Thr Tyr Pro Thr Asn Ala Thr Gly Thr Pro Gly Ala Ala Arg Gly Ser
385                 390                 395                 400 tgc cca acc acc tcg ggc gac ccc aag acc gtc gag agc cag agc ggc      1248
Cys Pro Thr Thr Ser Gly Asp Pro Lys Thr Val Glu Ser Gln Ser Gly
                405                 410                 415 agc agc tac gtg acc ttc agc gac atc cgc gtg ggc ccg ttc aac tcc      1296
```

```
Ser Ser Tyr Val Thr Phe Ser Asp Ile Arg Val Gly Pro Phe Asn Ser
            420                 425                 430 acg ttc agc ggt ggc tct agc acg ggc ggc tcc tcc acc acc acc gcc      1344
Thr Phe Ser Gly Gly Ser Ser Thr Gly Gly Ser Ser Thr Thr Thr Ala
            435                 440                 445 agc ggc acc acc acc aag gcc tcc agc acg tct act agc tcc acc          1392
Ser Gly Thr Thr Thr Lys Ala Ser Ser Thr Ser Thr Ser Ser Thr
            450                 455                 460 tct acc ggc acc ggc gtt gct gcc cat tgg ggc cag tgc ggt ggc cag      1440
Ser Thr Gly Thr Gly Val Ala Ala His Trp Gly Gln Cys Gly Gly Gln
465                 470                 475                 480 ggc tgg acg ggt cca acg act tgc gcc tcc ggc acc acc tgc acc gtg      1488
Gly Trp Thr Gly Pro Thr Thr Cys Ala Ser Gly Thr Thr Cys Thr Val
                485                 490                 495 gtc aat ccg tac tac tcc cag tgc ctg tga                              1518
Val Asn Pro Tyr Tyr Ser Gln Cys Leu *
                500                 505

<210> SEQ ID NO 15
<211> LENGTH: 505
<212> TYPE: PRT
<213> ORGANISM: Artificial Sequence
<220> FEATURE:
<223> OTHER INFORMATION: cellulobiohydrolase 1 sequence encoded by
      synthetic gene

<400> SEQUENCE: 15

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
    130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
    210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
```

```
                            245                 250                 255
Asp Gly Cys Asp Phe Asn Pro Tyr Arg Leu Gly Val Thr Asp Phe Tyr
                260                 265                 270

Gly Ser Gly Lys Thr Val Asp Thr Thr Lys Pro Ile Thr Val Val Thr
            275                 280                 285

Gln Phe Val Thr Asp Asp Gly Thr Ser Thr Gly Thr Leu Ser Glu Ile
        290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
        355                 360                 365

Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
            420                 425                 430

Thr Phe Ser Gly Gly Ser Ser Thr Gly Gly Ser Ser Thr Thr Thr Ala
        435                 440                 445

Ser Gly Thr Thr Thr Thr Lys Ala Ser Ser Thr Ser Ser Thr Ser Thr
450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
            500                 505

<210> SEQ ID NO 16
<211> LENGTH: 1368
<212> TYPE: DNA
<213> ORGANISM: Artificial Sequence
<220> FEATURE:
<223> OTHER INFORMATION: synthetic sequence encoding cellobiohydrolase 2
<221> NAME/KEY: CDS
<222> LOCATION: (1)...(1368)

<400> SEQUENCE: 16 atg gtg ccg ctc gag gaa agg cag agc tgc tcc tct gtc tgg ggt caa      48
Met Val Pro Leu Glu Glu Arg Gln Ser Cys Ser Ser Val Trp Gly Gln
 1               5                  10                  15 tgc ggt ggc cag aac tgg gct ggc ccg ttc tgc tgc gcc tcc ggt agc      96
Cys Gly Gly Gln Asn Trp Ala Gly Pro Phe Cys Cys Ala Ser Gly Ser
                20                  25                  30 acc tgc gtg tac tcc aac gac tac tac tcc cag tgc ctc ccc ggt acg     144
Thr Cys Val Tyr Ser Asn Asp Tyr Tyr Ser Gln Cys Leu Pro Gly Thr
            35                  40                  45 gcc agc agc agc agc tcc acg cgc gcc tcc agc acc acc tcc agg gtg     192
Ala Ser Ser Ser Ser Ser Thr Arg Ala Ser Ser Thr Thr Ser Arg Val
        50                  55                  60 tcc agc gcc acc tcc acc agg tcc tcc agc agc acc cca cca cct gcc     240
Ser Ser Ala Thr Ser Thr Arg Ser Ser Ser Ser Thr Pro Pro Pro Ala
```

-continued

|     |     |     |     |     |     |     |     |     |     |     |     |     |     |     |     |     |
|---|---|---|---|---|---|---|---|---|---|---|---|---|---|---|---|---|
| 65  |     |     |     |     | 70  |     |     |     |     | 75  |     |     |     |     | 80 |     |

```
agc tcc acc acc cca gcc cca gtg ggc agc ggc acg gcg acg tac       288
Ser Ser Thr Thr Pro Ala Pro Val Gly Ser Gly Thr Ala Thr Tyr
                    85                  90                  95 tcc ggc aac ccc ttc gcc ggc gtg acc cct tgg gcc aac agc ttc tac   336
Ser Gly Asn Pro Phe Ala Gly Val Thr Pro Trp Ala Asn Ser Phe Tyr
            100                 105                 110 gcc agc gag gtg tcc acc ctg gcc atc cca agc ctg acc ggc gct atg   384
Ala Ser Glu Val Ser Thr Leu Ala Ile Pro Ser Leu Thr Gly Ala Met
        115                 120                 125 gct acg gct gcg gcc gct gtg gcc aag gtg ccg agc ttc atg tgg ctg   432
Ala Thr Ala Ala Ala Ala Val Ala Lys Val Pro Ser Phe Met Trp Leu
    130                 135                 140 gac acg ctt gac aag acc ccg ctg atg agc agc acc ctg agc gac atc   480
Asp Thr Leu Asp Lys Thr Pro Leu Met Ser Ser Thr Leu Ser Asp Ile
145                 150                 155                 160 agg gcc gcc aac aag gct ggc ggc aac tac gcc ggc cag ttc gtg gtg   528
Arg Ala Ala Asn Lys Ala Gly Gly Asn Tyr Ala Gly Gln Phe Val Val
                    165                 170                 175 tac gac ctg ccg gac agg gac tgc gct gcc gct gcc tcc aat ggt gag   576
Tyr Asp Leu Pro Asp Arg Asp Cys Ala Ala Ala Ala Ser Asn Gly Glu
                180                 185                 190 tac tcc atc gcc gac ggc ggc gtg gcc aag tac aag aac tac atc gac   624
Tyr Ser Ile Ala Asp Gly Gly Val Ala Lys Tyr Lys Asn Tyr Ile Asp
            195                 200                 205 acc atc cgc ggc atc gtg acc acc ttc agc gat gtg cgc atc ctg ctg   672
Thr Ile Arg Gly Ile Val Thr Thr Phe Ser Asp Val Arg Ile Leu Leu
        210                 215                 220 gtg atc gag ccg gac agc ctg gcc aac ctg gtg acc aac ctg gcc acc   720
Val Ile Glu Pro Asp Ser Leu Ala Asn Leu Val Thr Asn Leu Ala Thr
225                 230                 235                 240 ccg aag tgc tcc aac gcc cag agc gcc tac ctc gag tgc atc aac tac   768
Pro Lys Cys Ser Asn Ala Gln Ser Ala Tyr Leu Glu Cys Ile Asn Tyr
                    245                 250                 255 gcc atc acc cag ctg aac ctg ccg aac gtg gcc atg tac ctg gac gcc   816
Ala Ile Thr Gln Leu Asn Leu Pro Asn Val Ala Met Tyr Leu Asp Ala
                260                 265                 270 ggc cac gcc ggt tgg ctt ggg tgg cca gcg aac cag gac cca gcc gcc   864
Gly His Ala Gly Trp Leu Gly Trp Pro Ala Asn Gln Asp Pro Ala Ala
            275                 280                 285 cag ctg ttc gcc aac gtg tac aag aac gcc agc agc ccg agg gct gtg   912
Gln Leu Phe Ala Asn Val Tyr Lys Asn Ala Ser Ser Pro Arg Ala Val
        290                 295                 300 agg ggc ctg gcc acc aac gtg gcc aac tac aac gcc tgg aac atc acc   960
Arg Gly Leu Ala Thr Asn Val Ala Asn Tyr Asn Ala Trp Asn Ile Thr
305                 310                 315                 320 acc ccg ccg agc tac acc cag ggc aac gcc gtg tac aac gag aag ctg   1008
Thr Pro Pro Ser Tyr Thr Gln Gly Asn Ala Val Tyr Asn Glu Lys Leu
                    325                 330                 335 tac atc cac gcc ctg ggc cca ctg ctg gcc aac cac ggc tgg tcc aac   1056
Tyr Ile His Ala Leu Gly Pro Leu Leu Ala Asn His Gly Trp Ser Asn
                340                 345                 350 gcc ttc ttc atc acc gac cag ggc cgc agc ggc aag cag cca acc ggc   1104
Ala Phe Phe Ile Thr Asp Gln Gly Arg Ser Gly Lys Gln Pro Thr Gly
            355                 360                 365 cag ctc gag tgg ggc aac tgg tgc aac gct gtg ggc acc ggc ttc ggc   1152
Gln Leu Glu Trp Gly Asn Trp Cys Asn Ala Val Gly Thr Gly Phe Gly
        370                 375                 380 atc agg ccg agc gcc aac acc ggc gac agc ctg ctg gac agc ttt gtg   1200
Ile Arg Pro Ser Ala Asn Thr Gly Asp Ser Leu Leu Asp Ser Phe Val
```

```
                    385                 390                 395                 400
tgg atc aag cca ggc ggc gag tgc gac ggc acc agc aac agc agc gcc          1248
Trp Ile Lys Pro Gly Gly Glu Cys Asp Gly Thr Ser Asn Ser Ser Ala
                    405                 410                 415 cca cgc ttc gac tac cac tgc gcc agc gcc gac gcc ctc cag cca gcc          1296
Pro Arg Phe Asp Tyr His Cys Ala Ser Ala Asp Ala Leu Gln Pro Ala
                420                 425                 430 cca cag gcc ggc agc tgg ttc cag gcc tac ttc gtc cag ctg ctg acc          1344
Pro Gln Ala Gly Ser Trp Phe Gln Ala Tyr Phe Val Gln Leu Leu Thr
                435                 440                 445 aac gcc aac ccg agc ttc ctg tga                                          1368
Asn Ala Asn Pro Ser Phe Leu  *
                450                 455

<210> SEQ ID NO 17
<211> LENGTH: 455
<212> TYPE: PRT
<213> ORGANISM: Artificial Sequence
<220> FEATURE:
<223> OTHER INFORMATION: cellulobiohydrolase 2 sequence encoded by
      synthetic gene

<400> SEQUENCE: 17

Met Val Pro Leu Glu Glu Arg Gln Ser Cys Ser Ser Val Trp Gly Gln
 1               5                  10                  15

Cys Gly Gly Gln Asn Trp Ala Gly Pro Phe Cys Cys Ala Ser Gly Ser
            20                  25                  30

Thr Cys Val Tyr Ser Asn Asp Tyr Tyr Ser Gln Cys Leu Pro Gly Thr
        35                  40                  45

Ala Ser Ser Ser Ser Thr Arg Ala Ser Ser Thr Thr Ser Arg Val
    50                  55                  60

Ser Ser Ala Thr Ser Thr Arg Ser Ser Ser Thr Pro Pro Ala
65                  70                  75                  80

Ser Ser Thr Thr Pro Ala Pro Pro Val Gly Ser Gly Thr Ala Thr Tyr
                85                  90                  95

Ser Gly Asn Pro Phe Ala Gly Val Thr Pro Trp Ala Asn Ser Phe Tyr
            100                 105                 110

Ala Ser Glu Val Ser Thr Leu Ala Ile Pro Ser Leu Thr Gly Ala Met
        115                 120                 125

Ala Thr Ala Ala Ala Val Ala Lys Val Pro Ser Phe Met Trp Leu
    130                 135                 140

Asp Thr Leu Asp Lys Thr Pro Leu Met Ser Ser Thr Leu Ser Asp Ile
145                 150                 155                 160

Arg Ala Ala Asn Lys Ala Gly Gly Asn Tyr Ala Gly Gln Phe Val Val
                165                 170                 175

Tyr Asp Leu Pro Asp Arg Asp Cys Ala Ala Ala Ser Asn Gly Glu
            180                 185                 190

Tyr Ser Ile Ala Asp Gly Gly Val Ala Lys Tyr Lys Asn Tyr Ile Asp
        195                 200                 205

Thr Ile Arg Gly Ile Val Thr Thr Phe Ser Asp Val Arg Ile Leu Leu
    210                 215                 220

Val Ile Glu Pro Asp Ser Leu Ala Asn Leu Val Thr Asn Leu Ala Thr
225                 230                 235                 240

Pro Lys Cys Ser Asn Ala Gln Ser Ala Tyr Leu Glu Cys Ile Asn Tyr
                245                 250                 255

Ala Ile Thr Gln Leu Asn Leu Pro Asn Val Ala Met Tyr Leu Asp Ala
            260                 265                 270
```

```
Gly His Ala Gly Trp Leu Gly Trp Pro Ala Asn Gln Asp Pro Ala Ala
            275                 280                 285

Gln Leu Phe Ala Asn Val Tyr Lys Asn Ala Ser Ser Pro Arg Ala Val
        290                 295                 300

Arg Gly Leu Ala Thr Asn Val Ala Asn Tyr Asn Ala Trp Asn Ile Thr
305                 310                 315                 320

Thr Pro Pro Ser Tyr Thr Gln Gly Asn Ala Val Tyr Asn Glu Lys Leu
                325                 330                 335

Tyr Ile His Ala Leu Gly Pro Leu Leu Ala Asn His Gly Trp Ser Asn
            340                 345                 350

Ala Phe Phe Ile Thr Asp Gln Gly Arg Ser Gly Lys Gln Pro Thr Gly
        355                 360                 365

Gln Leu Glu Trp Gly Asn Trp Cys Asn Ala Val Gly Thr Gly Phe Gly
    370                 375                 380

Ile Arg Pro Ser Ala Asn Thr Gly Asp Ser Leu Leu Asp Ser Phe Val
385                 390                 395                 400

Trp Ile Lys Pro Gly Gly Glu Cys Asp Gly Thr Ser Asn Ser Ser Ala
                405                 410                 415

Pro Arg Phe Asp Tyr His Cys Ala Ser Ala Asp Ala Leu Gln Pro Ala
            420                 425                 430

Pro Gln Ala Gly Ser Trp Phe Gln Ala Tyr Phe Val Gln Leu Leu Thr
        435                 440                 445

Asn Ala Asn Pro Ser Phe Leu
    450                 455

<210> SEQ ID NO 18
<211> LENGTH: 1467
<212> TYPE: DNA
<213> ORGANISM: Artificial Sequence
<220> FEATURE:
<223> OTHER INFORMATION: synthetic sequence encoding cellobiohydrolase 1
<221> NAME/KEY: CDS
<222> LOCATION: (1)...(1467)

<400> SEQUENCE: 18 atg cag caa gtg tgc acc cag cag gcc gag acc cac cca cca ctg acc    48
Met Gln Gln Val Cys Thr Gln Gln Ala Glu Thr His Pro Pro Leu Thr
1               5                   10                  15 tgg cag aag tgc acc gcc tct ggc tgc acg gcc cag agc ggc agc gtg    96
Trp Gln Lys Cys Thr Ala Ser Gly Cys Thr Ala Gln Ser Gly Ser Val
            20                  25                  30 gtg ctg gac gcc aac tgg cgc tgg acc cac gac acc aag agc acc acc    144
Val Leu Asp Ala Asn Trp Arg Trp Thr His Asp Thr Lys Ser Thr Thr
        35                  40                  45 aac tgc tac gac ggc aac acc tgg tcc agc acc ctg tgc cca gac gac    192
Asn Cys Tyr Asp Gly Asn Thr Trp Ser Ser Thr Leu Cys Pro Asp Asp
    50                  55                  60 gcc acc tgc gcc aag aac tgc tgt ctg gat ggt gcc aac tac tcc ggc    240
Ala Thr Cys Ala Lys Asn Cys Cys Leu Asp Gly Ala Asn Tyr Ser Gly
65                  70                  75                  80 acc tac ggc gtg acc acc tcc ggc gac gcc ctg acc atc cag ttc gtg    288
Thr Tyr Gly Val Thr Thr Ser Gly Asp Ala Leu Thr Ile Gln Phe Val
                85                  90                  95 acc cag agc aat gtg ggc agc cgc ctg tac ctg atg gcc acc gac acc    336
Thr Gln Ser Asn Val Gly Ser Arg Leu Tyr Leu Met Ala Thr Asp Thr
            100                 105                 110 acc tac cag gag ttc acc ctg agc ggc aac gag ttc agc ttc gac gtg    384
Thr Tyr Gln Glu Phe Thr Leu Ser Gly Asn Glu Phe Ser Phe Asp Val
        115                 120                 125
```

```
gac gtg tcc cag ctg ccc tgc ggc ctg aac ggc gcc ctg tac ttc gtg      432
Asp Val Ser Gln Leu Pro Cys Gly Leu Asn Gly Ala Leu Tyr Phe Val
    130             135                 140 tcg atg gat gct gac ggc ggc aag agc aag tac ccg ggc aac gcc gct      480
Ser Met Asp Ala Asp Gly Gly Lys Ser Lys Tyr Pro Gly Asn Ala Ala
145                 150                 155                 160 ggc gcc aag tac ggc acc ggc tac tgc gac agc cag tgc ccg agg gac      528
Gly Ala Lys Tyr Gly Thr Gly Tyr Cys Asp Ser Gln Cys Pro Arg Asp
                165                 170                 175 ctg aag ttc atc aac ggc cag gcc aac gtg gac ggc tgg caa ccc agc      576
Leu Lys Phe Ile Asn Gly Gln Ala Asn Val Asp Gly Trp Gln Pro Ser
            180                 185                 190 agc aac aac gcc aac acc ggc atc ggc aac cac ggc agc tgc tgc tcc      624
Ser Asn Asn Ala Asn Thr Gly Ile Gly Asn His Gly Ser Cys Cys Ser
        195                 200                 205 gag atg gac atc tgg gag gcc aac agc atc agc gag gcc ctg acc cca      672
Glu Met Asp Ile Trp Glu Ala Asn Ser Ile Ser Glu Ala Leu Thr Pro
    210                 215                 220 cac cca tgc gag gat gtg ggc cag acc atg tgc tcc ggc gac agc tgc      720
His Pro Cys Glu Asp Val Gly Gln Thr Met Cys Ser Gly Asp Ser Cys
225                 230                 235                 240 ggt ggc acc tac tcc gac gac aga tac ggt ggc act tgc gac cca gac      768
Gly Gly Thr Tyr Ser Asp Asp Arg Tyr Gly Gly Thr Cys Asp Pro Asp
                245                 250                 255 ggc tgc gac tgg aac cca tac aga ctg ggt aac acg agc ttc tac ggc      816
Gly Cys Asp Trp Asn Pro Tyr Arg Leu Gly Asn Thr Ser Phe Tyr Gly
            260                 265                 270 cca ggc agc agc ttc acc ctg gac acc acc aag aag ctg acc gtc gtc      864
Pro Gly Ser Ser Phe Thr Leu Asp Thr Thr Lys Lys Leu Thr Val Val
        275                 280                 285 acc cag ttc gcc acc aac ggc gcc atc agc cgc tac tac gtc cag aac      912
Thr Gln Phe Ala Thr Asn Gly Ala Ile Ser Arg Tyr Tyr Val Gln Asn
    290                 295                 300 ggc gtg aag ttc cag cag ccg aac gcc caa gtg ggc agc tac tcc ggc      960
Gly Val Lys Phe Gln Gln Pro Asn Ala Gln Val Gly Ser Tyr Ser Gly
305                 310                 315                 320 aac acc atc aac gcc gac tac tgc gct gcc gag cag acc gcc ttc ggc     1008
Asn Thr Ile Asn Ala Asp Tyr Cys Ala Ala Glu Gln Thr Ala Phe Gly
                325                 330                 335 ggc acc agc ttc acc gac aag ggc ggc ctg gcc cag atc aac aag gcc     1056
Gly Thr Ser Phe Thr Asp Lys Gly Gly Leu Ala Gln Ile Asn Lys Ala
            340                 345                 350 ttc cag ggc ggc atg gtg ctg gtg atg agc ctg tgg gac gac tac gcc     1104
Phe Gln Gly Gly Met Val Leu Val Met Ser Leu Trp Asp Asp Tyr Ala
        355                 360                 365 gtg aac atg ctg tgg ctg gac agc acc tac ccg gcc aac gcc acg ggt     1152
Val Asn Met Leu Trp Leu Asp Ser Thr Tyr Pro Ala Asn Ala Thr Gly
    370                 375                 380 acg cca ggc gcc aag agg ggc agc tgc tcc acc tcc agc ggc gtg cca     1200
Thr Pro Gly Ala Lys Arg Gly Ser Cys Ser Thr Ser Ser Gly Val Pro
385                 390                 395                 400 gcc cag gtg gag gcc cag agc ccg aac agc aag gtg gtg ttc agc aac     1248
Ala Gln Val Glu Ala Gln Ser Pro Asn Ser Lys Val Val Phe Ser Asn
                405                 410                 415 atc cgc ttc ggc ccg atc ggc agc acc ggc ggc aac acc ggc agc aac     1296
Ile Arg Phe Gly Pro Ile Gly Ser Thr Gly Gly Asn Thr Gly Ser Asn
            420                 425                 430 ccg cca ggc acc agc acc acc agg gcc cca cca agc tcc acg ggc agc     1344
Pro Pro Gly Thr Ser Thr Thr Arg Ala Pro Pro Ser Ser Thr Gly Ser
        435                 440                 445
```

```
agc cca acc gcc acc cag acc cac tac ggc caa tgc ggc ggc act ggc    1392
Ser Pro Thr Ala Thr Gln Thr His Tyr Gly Gln Cys Gly Gly Thr Gly
    450                 455                 460 tgg ggt ggc cca acc atc tgc gcc tcc ggc tac acc tgc cag gtg ctg    1440
Trp Gly Gly Pro Thr Ile Cys Ala Ser Gly Tyr Thr Cys Gln Val Leu
465                 470                 475                 480 aac ccg ttc tac tcc cag tgc ctg tga                                1467
Asn Pro Phe Tyr Ser Gln Cys Leu *
                485

<210> SEQ ID NO 19
<211> LENGTH: 488
<212> TYPE: PRT
<213> ORGANISM: Artificial Sequence
<220> FEATURE:
<223> OTHER INFORMATION: cellulobiohydrolase 1 sequence encoded by
      synthetic gene

<400> SEQUENCE: 19

Met Gln Gln Val Cys Thr Gln Ala Glu Thr His Pro Pro Leu Thr
 1               5                  10                  15

Trp Gln Lys Cys Thr Ala Ser Gly Cys Thr Ala Gln Ser Gly Ser Val
                20                  25                  30

Val Leu Asp Ala Asn Trp Arg Trp Thr His Asp Thr Lys Ser Thr Thr
            35                  40                  45

Asn Cys Tyr Asp Gly Asn Thr Trp Ser Ser Thr Leu Cys Pro Asp Asp
 50                  55                  60

Ala Thr Cys Ala Lys Asn Cys Cys Leu Asp Gly Ala Asn Tyr Ser Gly
65                  70                  75                  80

Thr Tyr Gly Val Thr Thr Ser Gly Asp Ala Leu Thr Ile Gln Phe Val
                85                  90                  95

Thr Gln Ser Asn Val Gly Ser Arg Leu Tyr Leu Met Ala Thr Asp Thr
            100                 105                 110

Thr Tyr Gln Glu Phe Thr Leu Ser Gly Asn Glu Phe Ser Phe Asp Val
        115                 120                 125

Asp Val Ser Gln Leu Pro Cys Gly Leu Asn Gly Ala Leu Tyr Phe Val
130                 135                 140

Ser Met Asp Ala Asp Gly Gly Lys Ser Lys Tyr Pro Gly Asn Ala Ala
145                 150                 155                 160

Gly Ala Lys Tyr Gly Thr Gly Tyr Cys Asp Ser Gln Cys Pro Arg Asp
                165                 170                 175

Leu Lys Phe Ile Asn Gly Gln Ala Asn Val Asp Gly Trp Gln Pro Ser
            180                 185                 190

Ser Asn Asn Ala Asn Thr Gly Ile Gly Asn His Gly Ser Cys Cys Ser
        195                 200                 205

Glu Met Asp Ile Trp Glu Ala Asn Ser Ile Ser Glu Ala Leu Thr Pro
210                 215                 220

His Pro Cys Glu Asp Val Gly Gln Thr Met Cys Ser Gly Asp Ser Cys
225                 230                 235                 240

Gly Gly Thr Tyr Ser Asp Asp Arg Tyr Gly Gly Thr Cys Asp Pro Asp
                245                 250                 255

Gly Cys Asp Trp Asn Pro Tyr Arg Leu Gly Asn Thr Ser Phe Tyr Gly
            260                 265                 270

Pro Gly Ser Ser Phe Thr Leu Asp Thr Thr Lys Lys Leu Thr Val Val
        275                 280                 285

Thr Gln Phe Ala Thr Asn Gly Ala Ile Ser Arg Tyr Tyr Val Gln Asn
290                 295                 300
```

```
Gly Val Lys Phe Gln Gln Pro Asn Ala Gln Val Gly Ser Tyr Ser Gly
305                 310                 315                 320

Asn Thr Ile Asn Ala Asp Tyr Cys Ala Ala Glu Gln Thr Ala Phe Gly
            325                 330                 335

Gly Thr Ser Phe Thr Asp Lys Gly Gly Leu Ala Gln Ile Asn Lys Ala
            340                 345                 350

Phe Gln Gly Gly Met Val Leu Val Met Ser Leu Trp Asp Asp Tyr Ala
        355                 360                 365

Val Asn Met Leu Trp Leu Asp Ser Thr Tyr Pro Ala Asn Ala Thr Gly
    370                 375                 380

Thr Pro Gly Ala Lys Arg Gly Ser Cys Ser Thr Ser Ser Gly Val Pro
385                 390                 395                 400

Ala Gln Val Glu Ala Gln Ser Pro Asn Ser Lys Val Val Phe Ser Asn
                405                 410                 415

Ile Arg Phe Gly Pro Ile Gly Ser Thr Gly Asn Thr Gly Ser Asn
            420                 425                 430

Pro Pro Gly Thr Ser Thr Thr Arg Ala Pro Pro Ser Ser Thr Gly Ser
            435                 440                 445

Ser Pro Thr Ala Thr Gln Thr His Tyr Gly Gln Cys Gly Gly Thr Gly
        450                 455                 460

Trp Gly Gly Pro Thr Ile Cys Ala Ser Gly Tyr Thr Cys Gln Val Leu
465                 470                 475                 480

Asn Pro Phe Tyr Ser Gln Cys Leu
                485

<210> SEQ ID NO 20
<211> LENGTH: 1467
<212> TYPE: DNA
<213> ORGANISM: Artificial Sequence
<220> FEATURE:
<223> OTHER INFORMATION: synthetic sequence encoding cellobiohydrolase 1
<221> NAME/KEY: CDS
<222> LOCATION: (1)...(1467)

<400> SEQUENCE: 20 atg caa caa gtg tgc act caa caa gct gag act cat cca cca ctt act    48
Met Gln Gln Val Cys Thr Gln Gln Ala Glu Thr His Pro Pro Leu Thr
  1               5                  10                  15 tgg caa aag tgc act gct tct gga tgc act gct cag tct gga tct gtt    96
Trp Gln Lys Cys Thr Ala Ser Gly Cys Thr Ala Gln Ser Gly Ser Val
             20                  25                  30 gtg ctt gat gcc aat tgg agg tgg act cac gat acc aag tct acc acc   144
Val Leu Asp Ala Asn Trp Arg Trp Thr His Asp Thr Lys Ser Thr Thr
         35                  40                  45 aac tgc tac gat gga aac act tgg tca tct acc ctt tgc cca gat gat   192
Asn Cys Tyr Asp Gly Asn Thr Trp Ser Ser Thr Leu Cys Pro Asp Asp
     50                  55                  60 gct act tgc gct aag aac tgc tgc ctt gat ggt gct aac tac tct gga   240
Ala Thr Cys Ala Lys Asn Cys Cys Leu Asp Gly Ala Asn Tyr Ser Gly
 65                  70                  75                  80 acc tac ggt gtt act acc tct ggt gat gct ctc acc att cag ttc gtg   288
Thr Tyr Gly Val Thr Thr Ser Gly Asp Ala Leu Thr Ile Gln Phe Val
                 85                  90                  95 acc cag tct aat gtt gga tct agg ctc tac ctt atg gct act gat acc   336
Thr Gln Ser Asn Val Gly Ser Arg Leu Tyr Leu Met Ala Thr Asp Thr
            100                 105                 110 acc tac caa gag ttc acc ctt tct gga aac gag ttc tcc ttc gat gtt   384
Thr Tyr Gln Glu Phe Thr Leu Ser Gly Asn Glu Phe Ser Phe Asp Val
        115                 120                 125
```

```
gat gtg tct caa ctt cca tgc gga ctt aac ggt gct ctt tac ttc gtg         432
Asp Val Ser Gln Leu Pro Cys Gly Leu Asn Gly Ala Leu Tyr Phe Val
    130             135             140 tct atg gat gct gat ggt ggc aag tct aag tat cca gga aat gct gct         480
Ser Met Asp Ala Asp Gly Gly Lys Ser Lys Tyr Pro Gly Asn Ala Ala
145             150             155             160 ggc gct aag tat gga act gga tac tgc gat tct caa tgc cca agg gac         528
Gly Ala Lys Tyr Gly Thr Gly Tyr Cys Asp Ser Gln Cys Pro Arg Asp
                165             170             175 ctc aag ttc att aac gga cag gct aac gtt gat gga tgg cag cca tct         576
Leu Lys Phe Ile Asn Gly Gln Ala Asn Val Asp Gly Trp Gln Pro Ser
            180             185             190 tct aac aac gct aac acc gga att gga aac cac gga tct tgc tgc tct         624
Ser Asn Asn Ala Asn Thr Gly Ile Gly Asn His Gly Ser Cys Cys Ser
        195             200             205 gag atg gat att tgg gag gct aac tcc att tct gag gct ctt act cca         672
Glu Met Asp Ile Trp Glu Ala Asn Ser Ile Ser Glu Ala Leu Thr Pro
    210             215             220 cat cca tgc gag gat gtt gga caa act atg tgc tct ggt gat tct tgc         720
His Pro Cys Glu Asp Val Gly Gln Thr Met Cys Ser Gly Asp Ser Cys
225             230             235             240 gga gga acc tac tct gat gat aga tac ggt gga acc tgc gat cca gat         768
Gly Gly Thr Tyr Ser Asp Asp Arg Tyr Gly Gly Thr Cys Asp Pro Asp
                245             250             255 gga tgt gat tgg aac cca tac agg ctt gga aac acc tct ttc tac gga         816
Gly Cys Asp Trp Asn Pro Tyr Arg Leu Gly Asn Thr Ser Phe Tyr Gly
            260             265             270 cca gga tct tct ttc acc ctc gac acc act aag aag ttg acc gtt gtt         864
Pro Gly Ser Ser Phe Thr Leu Asp Thr Thr Lys Lys Leu Thr Val Val
        275             280             285 act cag ttc gct acc aac ggt gct att tcc agg tac tac gtt cag aac         912
Thr Gln Phe Ala Thr Asn Gly Ala Ile Ser Arg Tyr Tyr Val Gln Asn
    290             295             300 ggc gtt aag ttc caa caa cct aac gct caa gtg gga tct tac tcc gga         960
Gly Val Lys Phe Gln Gln Pro Asn Ala Gln Val Gly Ser Tyr Ser Gly
305             310             315             320 aac acc atc aac gct gat tat tgc gct gct gaa caa act gct ttc gga        1008
Asn Thr Ile Asn Ala Asp Tyr Cys Ala Ala Glu Gln Thr Ala Phe Gly
                325             330             335 gga acc tct ttc act gat aag ggt gga ctc gct cag att aac aag gct        1056
Gly Thr Ser Phe Thr Asp Lys Gly Gly Leu Ala Gln Ile Asn Lys Ala
            340             345             350 ttc cag ggt gga atg gtg ctt gtt atg tcc ctc tgg gat gat tac gct        1104
Phe Gln Gly Gly Met Val Leu Val Met Ser Leu Trp Asp Asp Tyr Ala
        355             360             365 gtg aac atg ctt tgg ctc gat tct act tac cca gct aac gct act gga        1152
Val Asn Met Leu Trp Leu Asp Ser Thr Tyr Pro Ala Asn Ala Thr Gly
    370             375             380 act cca ggt gct aag aga gga tct tgc tct act tct tcc ggt gtt cca        1200
Thr Pro Gly Ala Lys Arg Gly Ser Cys Ser Thr Ser Ser Gly Val Pro
385             390             395             400 gct caa gtt gag gct cag tct cca aac tct aag gtg gtg ttc agt aac        1248
Ala Gln Val Glu Ala Gln Ser Pro Asn Ser Lys Val Val Phe Ser Asn
                405             410             415 att aga ttc gga cca att gga tct act ggt gga aac acc gga tct aac        1296
Ile Arg Phe Gly Pro Ile Gly Ser Thr Gly Gly Asn Thr Gly Ser Asn
            420             425             430 cca cca gga act tct act act agg gct cca cca tct tct act gga tct        1344
Pro Pro Gly Thr Ser Thr Thr Arg Ala Pro Pro Ser Ser Thr Gly Ser
        435             440             445
```

-continued

```
tct cca act gct acc caa act cat tac gga caa tgc gga gga act gga     1392
Ser Pro Thr Ala Thr Gln Thr His Tyr Gly Gln Cys Gly Gly Thr Gly
    450                 455                 460 tgg gga gga cca act att tgc gct tct gga tac acc tgc caa gtg ctc     1440
Trp Gly Gly Pro Thr Ile Cys Ala Ser Gly Tyr Thr Cys Gln Val Leu
465                 470                 475                 480 aac cca ttc tac tct cag tgc ctt tga                                 1467
Asn Pro Phe Tyr Ser Gln Cys Leu *
                485

<210> SEQ ID NO 21
<211> LENGTH: 488
<212> TYPE: PRT
<213> ORGANISM: Artificial Sequence
<220> FEATURE:
<223> OTHER INFORMATION: cellulobiohydrolase 1 sequence encoded by
      synthetic gene

<400> SEQUENCE: 21

Met Gln Gln Val Cys Thr Gln Ala Glu Thr His Pro Pro Leu Thr
 1               5                   10                  15

Trp Gln Lys Cys Thr Ala Ser Gly Cys Thr Ala Gln Ser Gly Ser Val
                20                  25                  30

Val Leu Asp Ala Asn Trp Arg Trp Thr His Asp Thr Lys Ser Thr Thr
            35                  40                  45

Asn Cys Tyr Asp Gly Asn Thr Trp Ser Ser Thr Leu Cys Pro Asp Asp
        50                  55                  60

Ala Thr Cys Ala Lys Asn Cys Cys Leu Asp Gly Ala Asn Tyr Ser Gly
65                  70                  75                  80

Thr Tyr Gly Val Thr Thr Ser Gly Asp Ala Leu Thr Ile Gln Phe Val
                85                  90                  95

Thr Gln Ser Asn Val Gly Ser Arg Leu Tyr Leu Met Ala Thr Asp Thr
            100                 105                 110

Thr Tyr Gln Glu Phe Thr Leu Ser Gly Asn Glu Phe Ser Phe Asp Val
        115                 120                 125

Asp Val Ser Gln Leu Pro Cys Gly Leu Asn Gly Ala Leu Tyr Phe Val
    130                 135                 140

Ser Met Asp Ala Asp Gly Gly Lys Ser Lys Tyr Pro Gly Asn Ala Ala
145                 150                 155                 160

Gly Ala Lys Tyr Gly Thr Gly Tyr Cys Asp Ser Gln Cys Pro Arg Asp
                165                 170                 175

Leu Lys Phe Ile Asn Gly Gln Ala Asn Val Asp Gly Trp Gln Pro Ser
            180                 185                 190

Ser Asn Asn Ala Asn Thr Gly Ile Gly Asn His Gly Ser Cys Cys Ser
        195                 200                 205

Glu Met Asp Ile Trp Glu Ala Asn Ser Ile Ser Glu Ala Leu Thr Pro
    210                 215                 220

His Pro Cys Glu Asp Val Gly Gln Thr Met Cys Ser Gly Asp Ser Cys
225                 230                 235                 240

Gly Gly Thr Tyr Ser Asp Asp Arg Tyr Gly Gly Thr Cys Asp Pro Asp
                245                 250                 255

Gly Cys Asp Trp Asn Pro Tyr Arg Leu Gly Asn Thr Ser Phe Tyr Gly
            260                 265                 270

Pro Gly Ser Ser Phe Thr Leu Asp Thr Thr Lys Lys Leu Thr Val Val
        275                 280                 285

Thr Gln Phe Ala Thr Asn Gly Ala Ile Ser Arg Tyr Tyr Val Gln Asn
    290                 295                 300
```

-continued

```
Gly Val Lys Phe Gln Gln Pro Asn Ala Gln Val Gly Ser Tyr Ser Gly
305                 310                 315                 320

Asn Thr Ile Asn Ala Asp Tyr Cys Ala Ala Glu Gln Thr Ala Phe Gly
                325                 330                 335

Gly Thr Ser Phe Thr Asp Lys Gly Gly Leu Ala Gln Ile Asn Lys Ala
            340                 345                 350

Phe Gln Gly Gly Met Val Leu Val Met Ser Leu Trp Asp Asp Tyr Ala
        355                 360                 365

Val Asn Met Leu Trp Leu Asp Ser Thr Tyr Pro Ala Asn Ala Thr Gly
    370                 375                 380

Thr Pro Gly Ala Lys Arg Gly Ser Cys Ser Thr Ser Ser Gly Val Pro
385                 390                 395                 400

Ala Gln Val Glu Ala Gln Ser Pro Asn Ser Lys Val Val Phe Ser Asn
                405                 410                 415

Ile Arg Phe Gly Pro Ile Gly Ser Thr Gly Gly Asn Thr Gly Ser Asn
            420                 425                 430

Pro Pro Gly Thr Ser Thr Thr Arg Ala Pro Pro Ser Ser Thr Gly Ser
        435                 440                 445

Ser Pro Thr Ala Thr Gln Thr His Tyr Gly Gln Cys Gly Gly Thr Gly
    450                 455                 460

Trp Gly Gly Pro Thr Ile Cys Ala Ser Gly Tyr Thr Cys Gln Val Leu
465                 470                 475                 480

Asn Pro Phe Tyr Ser Gln Cys Leu
                485
```

METHODS FOR ACCUMULATING HETEROLOGOUS POLYPEPTIDES IN PLANT STOVER UTILIZING A VACUOLE SORTING SIGNAL

RELATED APPLICATIONS

This application claims priority from U.S. Provisional application Ser. No. 61/024,844, filed Jan. 30, 2008 and also claims priority from U.S. Provisional application Ser. No. 61/047,692, filed Apr. 24, 2008, both of which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "71796_Sequence_Listing.txt", created on Jan. 23, 2009, and having a size of 64 kilobytes and is filed concurrently with the specification. The sequence listing contained in this ASCII formatted document is part of the specification and is herein incorporated by reference in its entirety.

FIELD OF THE INVENTION

This invention relates to plant molecular biology, particularly to methods and compositions for increasing expression and/or accumulation of a heterologous polypeptide in plant tissue.

BACKGROUND OF THE INVENTION

With the emergence of transgenic technologies, new ways to improve the agronomic performance of plants for food, feed, and processing applications have been devised. In addition, the ability to express foreign genes using transgenic technologies has opened up options for producing large quantities of commercially important products in plants.

New target genes of both plant and microbial origin are rapidly becoming available for the purpose of improving agronomic characteristics of crop species as well as plant properties. These advancements have already resulted in the development of plants with desirable traits such as resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

SUMMARY OF THE INVENTION

Compositions and methods for increasing the expression and/or accumulation of polypeptides of interest in the vacuoles of plant cells are provided. The method involves targeting the polypeptide to the vacuoles through the use of a vacuole sorting signal peptide such as the barley polyamine oxidase (BPAO) vacuole sorting signal peptide. Plants transformed with an expression construct encoding the vacuole sorting signal peptide operably linked to the polypeptide of interest are predicted to direct expression of the polypeptide to the vacuoles of the plant cells.

Transgenic plants, seeds, and plant tissues, and plant parts are provided. Further provided are methods for high level expression and recovery of a polypeptide of interest from the vacuoles of a plant cell.

Downstream uses of transgenic plants or plant material comprising the expression constructs of the invention include agronomical and industrial uses, for example, human food, animal feed, biofuel, industrial alcohol, fermentation feedstocks, and the like.

DETAILED DESCRIPTION OF THE INVENTION

Overview

Methods and compositions are provided for increasing the expression and/or accumulation of a polypeptide of interest in the vacuoles of a plant cell. The method comprises introducing into the plant cell a nucleic acid construct comprising a vacuolar sorting signal sequence, such as the barley polyamine oxidase (BPAO) vacuole sorting signal sequence, operably linked to a nucleotide sequence encoding the polypeptide of interest. In various embodiments, the vacuole sorting signal sequence leads to an increase in the expression and/or accumulation of the polypeptide of interest in the vacuoles of a plant cell.

The vacuolar sorting signal sequences of the invention, when operably linked to a nucleotide sequence encoding a polypeptide of interest and expressed in a plant cell, function to direct or sort the encoded protein from within the ER to the vacuole of the plant cell. The term "vacuole sorting signal sequence" or "vacuole targeting sequence" as used herein refers to a nucleotide sequence encoding a vacuole targeting peptide sequence operable to direct or sort a selected protein to which such sequence is linked, to a plant vacuole.

The vacuoles of plants are a component of the secretory system of plant cells. Vacuoles store both polypeptides and secondary metabolites. A variety of polypeptides are stored in vacuoles such as degradative enzymes in autophagic or lytic vacuoles or proteins such as in seed storage vacuoles or vacuoles containing vegetative storage proteins. Vacuoles are frequently characterized by their function and are referred to as protein storage vacuoles or lytic vacuoles. Protein storage vacuoles are associated with several tissue types including leaves and seeds. In the seed, protein storage vacuoles may contain seed storage proteins. Lytic vacuoles are associated with the normal metabolic process of degrading and recycling proteins made by the cell. Lytic vacuoles frequently contain lytic enzymes such as peptidases which function in the breakdown of proteins.

Biomarkers effective for identifying the different types of vacuoles, lytic or storage, have been identified. Jauh et al, Plant Cell 11: 1867-1882 (1999) used confocal microscopy to characterize vacuoles and their expression of three tonoplast intrinsic proteins (TIPs). Three different types of vacuoles were identified based upon TIP content with seed storage vacuoles identified by either alpha and omega TIPs or alpha, omega and gamma TIPs. Vegetative storage vacuoles were identified by omega or omega and gamma TIPs. Lytic vacuoles were marked by gamma TIP. Interestingly, there is evidence that vacuoles can sub-compartmentalize and thus separate storage and lytic functions within the same vacuole. Paris et al, Cell 85(4): 563-572 (1996) describe a plant cell vacuole in which characterization of the tonoplast intrinsic proteins indicate that the vacuole has two different compartments, one compartment containing markers for storage proteins and the other compartment containing markers for lytic activity. See also Martinoia et al, J of Exp Botany 58(1): 83-102 (2007).

Since the vacuole of plant cells has a storage function, proteins directed there remain there, continually increasing in abundance, unless subject to degradation by vacuolar proteinases. Proteins stored in the vacuole are also isolated away from the major metabolic processes in the plant and thus will not interfere with the plant growth and development. Several reviews of vacuolar sorting signals have been published including Bethke and Jones, Current Opinion in Plant Biology 3:469-475 (2000); Nakamura and Matsuoka, Plant Physiol 101: 1-5 (1993); and Vitale and Hinz, Trends in Plant Sci 10: 316-323 (2005).

Three different types of vacuolar sorting signal peptides in plants have been identified. One type is an amino-terminal pro-peptide which has a known consensus sequence. A second type of vacuolar sorting signal peptide is a carboxy-terminal pro-peptide and the third type of signal are structural domains that exist within the mature protein. The instant application focuses on the use of either amino-terminal or carboxy-terminal pro-peptide sequences which target polypeptides to the vacuole of plant cells. While a consensus sequence for the carboxy-terminal vacuolar sorting signal peptides has not been identified, several examples exist including sequences from the barley polyaminoxidase 2 protein (Cervelli et al, The Plant Journal 40:410-418 (2004)), the tobacco proteinase inhibitor Na-PI (Miller et al, The Plant Cell 11:1499-1508 (1999)), the potato 20 kDa potato-tuber protein PT20 (Koide et al, Plant Cell Physiol 40:1152-1159 (1999)), barley lectin (Bednarek et al, Plant Cell 2:1145-1155 (1990)), tobacco chitinase A (Neuhaus et al, Proc Natl Acad Sci USA 88:10362-10366 (1991)); glucanase from tobacco (Sticher et al, Planta 188:559-565 (1992)); 2S albumin storage protein from Brazil nut (Saalbach et al, Plant Cell 3:695-708 (1991); Kirsch et al, Plant Physiol 111:469-474 (1996)); and 2S albumin storage protein from pea (Higgins et al, J Biol Chem 261:11124-11130 (1986)).

Examples of the amino-terminal vacuolar sorting signal peptides include sweet potato sporamin and tobacco sporamin (Matsuoka et al, J Biol Chem 265:19750-16757 (1990)), and barley aleurain (Holwerda et al, Plant Cell 4:307-318 (1992)).

The type of vacuolar sorting signal peptide, either amino-terminal or carboxy-terminal, does not always correlate with the type of vacuole (lytic or storage) to which the the signal peptide will direct sorting of polypeptides (Neuhaus et al Plant Molecular Biology 38:127-144 (1998)). There may be tissue type differences in the types of vacuoles present and where proteins traffic in these tissue types. As an example, root tip cells contain at least two types of vacuoles, one containing aleurain (amino-terminal sorting signal) and the other containing barley lectin (carboxy-terminal sorting signal) (Paris et al, Cell 85:563-572 (1996)). By contrast, in mature plant tissue barley lectin (carboxy-terminal sorting signal) and sporamin (amino-terminal sorting signal) are found in the same vacuole (Schroeder et al Plant Physiol 101:451-458 (1993)).

In addition, the different vacuolar sorting signals (amino-terminal versus carboxy-terminal) can function when placed in the opposite location as demonstrated in tobacco. The amino-terminal vacuolar sorting signal from sporamin was functional when placed at the carboxy-terminal end of a heterologous protein and expressed in transgenic tobacco (Koide et al Plant Physiol 114: 863-870 (1997)).

In one embodiment of the present invention, the vacuole sorting signal sequence is derived from the barley polyamine oxidase 2 (BPAO2) signal sequence. BPAO2 has an N-terminal signal peptide for entry into the secretory pathway. The presence of a C-terminal extension of the polypeptide results in vacuolar localization of BPAO in a plant cell (see Cervelli et al. The Plant Journal 40:410-418 (2004)). We believe the BPAO vacuole sorting signal sequence targets proteins to a protein storage vacuole or to the protein storage compartment of a vacuole that may contain separate compartments for storage and lytic functions. In one embodiment, the vacuole sorting signal sequence is set forth in SEQ ID NO:1. In another embodiment, the vacuole sorting signal sequence encodes SEQ ID NO:2. In yet another embodiment, the vacuole sorting signal sequence encodes a biologically-active fragment of the vacuole sorting peptide that is at least 5, at least 6, or at least 7 contiguous amino acids of SEQ ID NO:2. A "biologically-active" fragment of the vacuole sorting peptide is a peptide that is sufficient for targeting a polypeptide of interest to the vacuole of a plant cell.

In various embodiments, the nucleic acid constructs encoding the vacuole-targeted polypeptides described herein result in an increased expression and/or accumulation of the polypeptide in the vacuoles of the plant cell when compared to a control nucleic acid construct. By "control" nucleic acid construct is intended a nucleic acid construct comprising a vacuolar sorting signal sequence other than the BPAO (or functional fragment thereof) sequence described herein operably linked to a nucleotide sequence encoding the polypeptide of interest. Unless otherwise specified, the control vacuolar sorting signal sequence is the signal sequence set forth in SEQ ID NO:5. In one embodiment, the increase is at least about 2-fold, at least about 3-fold, at least about 4-fold, at least about 5-fold, at least about 6-fold, at least about 7-fold, at least about 10-fold, at least about 20-fold, or greater.

In another embodiment of the invention, the vacuole sorting signal peptide is operably linked to a polynucleotide encoding a heterologous polypeptide of interest wherein the vacuole sorting signal peptide directs the polypeptide to a plant vacuole. Enzymes can be a heterologous polypeptide of interest and are further defined below. An enzyme can be derived from any source such as a plant, bacteria, fungi or insect. The enzyme may be secreted by the native host cell. The enzyme can be a cellulase. It is further envisioned that the cellulase can be derived from a microorganism and may belong to any class of cellulase such as cellobiohydrolase I, cellobiohydrolase II or endoglucanase. The cellobiohydrolase I can be encoded by the polypeptide of any one of SEQ ID NOs: 11, 15, 19, or 21. The cellobiohydrolase II can be encoded by the polypeptide of any one of SEQ ID NOs: 13 or 17.

Thus, the methods of the invention find particular use in the integration of current practices for the cultivation of crop plants for the purpose of obtaining a commercially desired plant material with increased accumulation of certain polypeptides in the vacuoles of the plant cells, and the use of the crop plant residues as a source of biomass for the production of fermentable sugars, or for agricultural and/or human consumption.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, oats, tobacco, *Miscanthus* grass, Switch grass, trees, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses.

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The plant cell may be a part of the green tissue of the plant wherein the green tissue is composed of chlorophyll containing cells such as those in the leaves, stems, stalks, or shoots. Alternatively, the plant cell may be dessicated, dried, dehydrated or senescent plant tissue such as occurs in the formation of stover. Stover refers to tissue that remains after a plant has gone through the senescence process which is typically associated with tissues that remain after harvest has occurred.

In one embodiment, the plant is an indeterminate plant. These varieties grow vegetatively for indefinite periods in temperate regions. These varieties can be engineered to accumulate the polypeptide of interest in the vacuoles and can be grown until the first frost. At that time, the plant could be allowed to dessicate, then harvested dry, and used for food, livestock feed, or in biomass conversion processes.

As used herein, "biomass" refers to useful biological material including a product of interest, which material is to be collected and is intended for further processing to isolate or concentrate the product of interest. "Biomass" may comprise the fruit or parts of it or seeds, leaves, or stems or roots where these are the parts of the plant that are of particular interest for the industrial purpose. "Biomass", as it refers to plant material, includes any structure or structures of a plant that contain or represent the product of interest.

In another embodiment, vacuole targeted polypeptides remain in the plant tissue after the plant senesces and the tissue is dried down to form stover. This is a remarkable observation as the process of senescence in plants involves the breakdown of cellular components within degradative vacuoles in an autophagic process (Nooden in Nooden and Leopold, Chapter 1, The Phenomena of Senescence and Aging in Senescence and Aging in Plant (1988), Academic Press, Inc). The described method of producing vacuolar-targeted polypeptides in which the polypeptide is still present in senescent plant tissue is a significant divergence from the normal physiological changes associated with senescence. In another embodiment, the vacuolar-targeted polypeptide accumulates in stover and the polypeptide retains activity. In another embodiment, the vacuolar-targeted polypeptide in stover retains at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10% of the level of activity of the vacuolar-targeted polypeptide measured in green tissue. Alternatively, the vacuolar-targeted polypeptide in stover increases in activity by at least 2 fold, at least 3 fold, at least 4 fold, at least 5 fold, at least 6 fold, at least 8 fold, at least 10 fold, at least 12 fold, at least 14 fold or at least 16 fold as compared to the activity measured in green tissue. Activity can be measured as a function of the activity of the polypeptide per unit of plant tissue or measured as a function of the activity of the polypeptide per unit of protein. In another embodiment, the vacuolar-targeted polypeptide is a protein that is secreted by the normal host for that protein. In another embodiment, the enzyme contains one or more features of the group consisting of internal disulfide bonds, glycosylation by the native host and glycosylation by the heterologous host. In another embodiment, the secreted protein is an enzyme. In another embodiment, the secreted protein is an enzyme expressed by a microorganism such as a fungi or bacteria. In another embodiment, the enzyme is a cellulase. In another embodiment, the cellulase is selected from the group consisting of CBH1 and CBH2. The CBH1 may be encoded by any one of the polypeptides of SEQ ID NOs: 11, 15, 19, or 21. The CBH2 may be encoded by any one of the polypeptides of SEQ ID NOs: 13 or 17.

In another embodiment, the vacuole targeted polypeptide remains stable in the stover tissue once the stover tissue has been collected. The heterologous polypeptide may be stable for at least 2 to 3 months, 3 to 6 months, 6 to 9 months, 9 months to a 1, or more than 1 year.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Use

Targeting of proteins to plant vacuoles is a useful strategy for producing commercial quantities of a desired protein. Plant vacuoles represent the largest compartment in the plant cell for dissolved substances. The most important storage proteins of tubers, bulbs, roots and stems, for example, are located in the vacuoles of the cells that compose those organs. Moreover, the storage proteins of most seeds are located in so-called protein bodies, which are specialized vacuoles to which the same sorting signals would seem to apply as to the vacuoles of the vegetative organs. It would therefore be advantageous to be able to direct proteins associated with an improvement in a plant's nutrient content specifically into the vacuole.

Similar considerations also apply to proteins that are degradative or may be toxic to the plant itself.

Thus, useful polypeptides for targeting to the vacuoles of a plant cell include those that are functional in downstream agronomical and industrial uses, such as human food, animal feed, biofuel, industrial alcohol, fermentation feedstock, and the like.

In one embodiment, plant material harvested from the transgenic plants described herein can be used to formulate food or beverage for human consumption or animal feed, can be used to formulate diet with easily digestible starch and hence more extractable energy, or can be used to improve the nutritional quality of the food or feed (e.g., increased vitamin content, increased oil content, increased protein content, etc). The food, feed, or beverage can be flour, dough, bread, pasta, cookies, cake, thickener, beer, malted beverage, or a food additive. The food, feed, or beer product of can have reduced allergenicity and/or increased digestibility. Further, a dough product can have increased strength and volume in comparison to a dough made from a non-transgenic seed or grain of the same species. The food, feed, or beverage can have hyper-digestible protein and/or hyperdigestible starch. The food, feed, or beverage can be hypoallergenic.

Oil extracted from the harvested plant material of the invention can be used as a raw material for chemical modification, a component of biodegradable material, a component of a blended food product, a component of an edible oil or cooking oil, lubricant or a component thereof, biodiesel or a component thereof, a component of a snack food, a fermentation process raw material, or a component of cosmetics.

The harvested plant material of the invention can also be combined with other ingredients to produce a useful product. The specific ingredients included in a product will be determined according to the ultimate use of the product. Exemplary products include animal feed, raw material for chemical modification, biodegradable materials, blended food product, edible oil, cooking oil, lubricant, biodiesel process raw material, snack food, cosmetics, cleaning and detergent compositions (e.g., laundry detergents, dish washing detergents, and hard surface cleaning compositions), and fermentation process raw material. Products incorporating the harvested plant material described herein also include complete or partially complete swine, poultry, and cattle feeds, pet foods, and human food products such as extruded snack foods, breads, as a food binding agent, aquaculture feeds, fermentable mixtures, food supplements, sport drinks, nutritional food bars, multi-vitamin supplements, diet drinks, and cereal foods. Products incorporating the harvested plant material described herein include, e.g., cardboard, paper products, and industrial materials. These products may incorporate the raw harvested plant material, or may incorporate a processed or extracted form of the harvested plant material (e.g., oil, protein, starch, etc. extracted from the harvested plant material).

Polypeptides of Interest

Polypeptides of interest that are suitable for vacuole-targeting and accumulation include those that improve or otherwise facilitate the conversion of harvested plant material into a commercially useful product, including, for example, increased or altered carbohydrate content and/or distribution, improved fermentation properties, increased oil content, increased protein content, improved digestability, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, soybean trypsin inhibitor, or starch degrading enzymes, depending on the downstream use. By "resulting in" or "contributing to" is intended that the polypeptide of interest can directly or indirectly contribute to the existence of a trait of interest (e.g., increasing cellulose degradation by the heterologous expression of a starch degrading enzyme).

In one embodiment, the vacuole-targeted polypeptide of interest contributes to improved digestibility for food or feed. Xylanases are hemicellulolytic enzymes that improve the breakdown of plant cell walls which leads to better utilization of the plant nutrients by the animal. This leads to improved growth rate and feed conversion. Also, the viscosity of the digesta derived from feeds containing xylan can be reduced as a result of xylanase activity.

Numerous xylanases from fungal and bacterial microorganisms have been identified and characterized. (See, e.g., U.S. Pat. No. 5,437,992; Coughlin, M. P.; Biely, P. et al., Espoo 1993; P. Souminen and T. Reinikainen eds., Foundation for Biotechnical and Industrial Fermentation Research 8:125-135 (1993); U.S. Patent Application Publication No. 2005/0208178; and WO03/16654). In particular, three specific xylanases (XYL-I, XYL-II, and XYL-III) have been identified in T. reesei (Tenkanen, et al., Enzyme Microb. Technol. 14:566 (1992); Torronen, et al., Bio/Technology 10: 1461 (1992); and Xu, et al., Appl. Microbiol. Biotechnol. 49:718 (1998)).

In another embodiment, the vacuole-targeted polypeptide of interest is a polysaccharide degrading enzyme. Such plants may be useful for generating, for example, fermentation feedstocks for bioprocessing. In some embodiments, the enzymes useful for fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as $\alpha$-amylases (EC 3.2.1.1), glucuronidases (E.C. 3.2.1.131); exo-1,4-$\alpha$-D glucanases such as amyloglucosidases and glucoamylase (EC 3.2.1.3), $\beta$-amylases (EC 3.2.1.2), $\alpha$-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-$\beta$-D-glucanase (EC 3.2.1.39), $\beta$-glucosidase (EC 3.2.1.21); c) L-arabinases, such as endo-1,5-$\alpha$-L-arabinase (EC 3.2.1.99), $\alpha$-arabinosidases (EC 3.2.1.55) and the like; d) galactanases such as endo-1,4-$\beta$-D-galactanase (EC 3.2.1.89), endo-1,3-$\beta$-D-galactanase (EC 3.2.1.90), $\alpha$-galactosidase (EC 3.2.1.22), $\beta$-galactosidase (EC 3.2.1.23) and the like; e) mannanases, such as endo-1,4-$\beta$-D-mannanase (EC 3.2.1.78), $\beta$-mannosidase (EC 3.2.1.25), $\alpha$-mannosidase (EC 3.2.1.24) and the like; f) xylanases, such as endo-1,4-$\beta$-xylanase (EC 3.2.1.8), $\beta$-D-xylosidase (EC 3.2.1.37), 1,3-$\beta$-D-xylanase, and the like; g) other enzymes such as $\alpha$-L-fucosidase (EC 3.2.1.51), $\alpha$-L-rhamnosidase (EC 3.2.1.40), levanase (EC 3.2.1.65), inulanase (EC 3.2.1.7), and the like.

Another embodiment of the present invention encompasses the expression and accumulation of heterologous starch degrading enzymes such as glucoamylase and amylase in the harvested plant material for downstream use in, for example, ethanol production. Glucoamylases ($\alpha$-1,4-glucan glucohydrolases, E.C.3.2.1.3.) are starch hydrolyzing exo-acting carbohydrases. Glucoamylases catalyze the removal of successive glucose units from the non-reducing ends of starch or related oligo and polysaccharide molecules and can hydrolyze both linear and branched glucosidic linkages of starch (amylose and amylopectin). The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-$\alpha$-D-glucosidic linkages in polysaccharides containing 1,4-$\alpha$-linked D-glucose units. Another term used to describe these enzymes is "glycogenase." Exemplary enzymes include alpha-1,4-glucan 4-glucanohydrase glucanohydrolase. Commercially, glucoamylases and amylases are very important enzymes that have been used in a wide variety of applications requiring the hydrolysis of starch.

Further additional enzymes which may be used include proteases, such as fungal and bacterial proteases. Fungal proteases include, for example, those obtained from *Aspergillus, Trichoderma, Mucor* and *Rhizopus*, such as *A. niger, A. awamori, A. oryzae* and *M. miehei*. Of particular interest in the present invention are cellobiohydrolase (CBH) enzymes (EC 3.2.1.91). Cellulases are enzymes capable of hydrolyzing the 1,4-beta-D-glycosidic linkages in cellulose. In one embodiment, the cellobiohydrolase enzyme is CBH1 or CBH2, e.g., the CBH1 enzyme set forth in SEQ ID NO:11 and the CBH2 enzyme set forth in SEQ ID NO:13.

Other enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

The choice of enzymes may depend on the substrate specificity and/or the desired end-product for downstream use (e.g., enzymes with improved properties such as thermostability, acid stability, and the like). It will be recognized that any enzyme known in the art to perform one of the desired functions described herein can be used in the constructs of the invention. In one embodiment, the polypeptide of interest is encoded by the polynucleotide sequences set forth in SEQ ID NO:10, 12, 14, 16, 18, and 20.

It will also be recognized that the nucleotide sequence encoding the vacuolar sorting peptide, the polypeptide of interest, or both, may be optimized for increased expression in the transformed host cell. That is, the nucleotide sequences can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Polypeptides of interest may also be further modified or evolved from the original form appearing in nature in order to alter properties of the polypeptide of interest. There are several techniques or means available for evolving proteins to create variants with altered characteristics or properties. For example, techniques based upon random amino acid changes or random mutagenesis include chemical mutagenesis (Smith, Ann. Rev. Genet. 19:423-462 (1985)), DirectEvolution; (U.S. Pat. No. 5,830,696); Gene Site Saturation Mutagenesis (GSSM) (U.S. Pat. Nos. 6,171,820 and 6,579,258), Exonuclease-Mediated Gene Assembly in Directed Evolution (U.S. Pat. Nos. 6,361,974 and 6,352,842), End Selection in Directed Evolution (U.S. Pat. Nos. 6,358,709 and 6,238,884), Recombination-Based Synthesis Shuffling (U.S. Pat. Nos. 5,965,408 and 6,440,668, and Australian Patent No. AU724521), and Directed Evolution of Thermophilic Enzymes (U.S. Pat. Nos. 5,830,696 and 6,335,179). These techniques give rise to a pool of variants with random mutations and this pool of variants is then screened to identify those individual variants with the desired set of characteristics.

The characteristics of a protein which can be altered by evolution include the activity profile (i.e. optimum temperature, pH, salt concentration, ions, etc.). The new characteristics sought can be in addition to the proteins current set of characteristics or could involve altering a characteristic. Protein characteristics can include, but are not limited to, features of the activity profile, ability to absorb water, ability to prevent water absorption, gelling capacity, etc. For example, it may be desired to engineer a protein that displays thermotolerance and acid stability with the additional characteristic of enhanced susceptibility to protease digestion. In this example, the original characteristics of the protein (thermotolerance and acid stability) need to be maintained while the new characteristic (enhanced sensitivity to a protease) is added. One may also take into account the specific activity of an enzyme where "specific activity" of an enzyme being defined as the amount of substrate an enzyme is able to convert or catalyze over a given unit of time.

Plant Expression Cassettes

The compositions of the invention also comprise nucleic acid sequences for transformation and expression and accumulation of a polypeptide of interest in the vacuoles of a plant cell of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest (i.e., a nucleotide sequence encoding a polypeptide of interest) which is operatively linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of directing expression and accumulation of a polypeptide of interest in the vacuoles of a plant cell. The expression cassette will include in the 5'-3' direction of transcription, a transcriptional and translational initiation region (i.e., a promoter), a polynucleotide encoding a vacuolar sorting peptide, and a polynucleotide encoding a polypeptide of interest. The expression cassette may optionally comprise a transcriptional and translational termination region (i.e. termination region) functional in plants.

In addition to the polynucleotide sequence encoding the vacuolar sorting peptide, the construct may further comprise additional regulatory elements to facilitate transcription, translation, or transport of the polypeptide of interest. The regulatory sequences of the expression construct are operably linked to the polynucleotide of interest. By "operably linked" is intended a functional linkage between a regulatory element and a second sequence wherein the regulatory element initiates and/or mediates transcription, translation, or translocation of the DNA sequence corresponding to the second sequence. Generally, operably linked means that the nucleotide sequences being linked are contiguous. The regulatory elements include promoters, enhances, and signal sequences useful for targeting cytoplasmically-synthesized proteins to the endomembrane system of the plant cell. In one embodiment, the construct comprises, in the 5' to 3' direction of transcription, a transcriptional and translational initiation region (i.e., a promoter), a polynucleotide encoding an endoplastic reticulum signal sequence, a polynucleotide encoding a vacuolar sorting peptide, and a polynucleotide encoding a polypeptide of interest. Exemplary signal sequences include the gamma zein 27 kD signal sequence (SEQ ID NO:8) and the *Glycine max* glycinin-1 (GY1) signal sequence (SEQ ID NO:3). Others useful in the methods of the invention will be apparent to one of skill in the art.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996).

Promoters active in photosynthetic tissue in order to drive transcription in green tissues such as leaves and stems are of particular interest for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) Plant Cell Physiol. 35:773-778), the Cab-1 gene promoter from wheat (Fejes et al. (1990) Plant Mol. Biol. 15:921-932), the CAB-1 promoter from spinach (Lubberstedt et al. (1994) Plant Physiol. 104:997-1006), the cab1R promoter from rice (Luan et al. (1992) Plant Cell 4:971-981), the pyruvate orthophosphate dikinase (PPDK) promoter from corn (Matsuoka et al. (1993) Proc Natl Acad Sci USA 90:9586-9590), the tobacco Lhcb1*2 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346. The TrpA promoter is a pith preferred promoter and has been described in U.S. Pat. No. 6,018,104.

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a green tissue-specific manner in transgenic plants.

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

In some embodiments, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gelirke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Plants

Plants useful in the present invention include plants that are transgenic for at least a polynucleotide encoding a vacuole-targeted polypeptide of interest. One of skill in the art will recognize that plants may express one or more additional polypeptide sequences associated with or contributing to one or more secondary trait(s) of interest. These polypeptide may be cytoplasmically-expressed, may be targeted to a subcellular organelle, or may be secreted by the plant cell. Secondary traits of interest include agronomic traits that primarily are of benefit to a seed company, a grower, or a grain processor, for example, herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. A secondary trait of interest may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). A plethora of genes useful for generating plants with desired secondary traits are available in the art.

The type of plant selected depends on a variety of factors, including for example, the downstream use of the harvested plant material, amenability of the plant species to transformation, and the conditions under which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss.

It is further contemplated that the constructs of the invention may be introduced into plant varieties having improved properties suitable or optimal for a particular downstream use.

For example, naturally-occurring genetic variability in plants with altered starch metabolism are useful in the methods of the invention. Many such plants carry mutations in genes encoding isoforms of starch synthesis or starch degradation enzymes. For example, plants have been identified which are heterozygous or homozygous for one or more of the waxy (wx), amylose extender (ae), dull (du), horny (h), shrunken (sh), brittle (bt), floury (fl), opaque (o), or sugary (su) mutant alleles. See, for example, U.S. Pat. Nos. 4,428,972; 4,767,849; 4,774,328; 4789738; 4,789,557; 4,790,997; 4,792,458; 4,798,735; and 4,801,470, herein incorporated by reference. These plants can be used in their native form, or can be modified to exhibit one or more additional primary traits of interest.

For plants with increased nutritional quality, several varieties of corn are available, such as those with increased lysine (Crow's Hybrid Corn Company, Milford, Ill.), protein (BASF) and oil (Pfister Hybrid Corn Company, El Paso, Ill. under the trademark KERNOIL®) levels. Other suitable high oil corn includes the corn populations known as Illinois High Oil (IHO) and Alexander High Oil (Alexo), samples of which are available from the University of Illinois Maize Genetics Cooperative—Stock Center (Urbana, Ill.).

Sweet corn is also available in which there is a reduction in the amount of starch and an increase in the amount of glucose, sucrose and/or water soluble polysaccharides normally found in the immature corn kernel (Creech, R. and Alexander, D. E. In Maize Breeding and Genetics; D. B. Walden, Ed.; John Wiley and Sons: New York, 1978; pp. 249-264). In several plant species such as corn (Shannon & Garwood, 1984), pea (Bhattacharyya et al., 1990), potato (Hovenkamp-Hermelink et al., 1987), *Arabidopsis* (Caspar et al., 1985; Lin et al., 1988a; Lin et al., 1988b) and tobacco (Hanson et al., 1988), mutants with an altered carbohydrate composition have been found. Brown mid rib (Bmr) corn has been used as an alternative for improving digestibility for silage hybrids for decades. The improvement in ruminal intakes and digestibility is derived from reduced lignin content in Bmr mutated hybrids. Additional varieties, both naturally-occurring and transgenic, with desired traits that are useful for downstream processing as described herein are well known to those of skill in the art.

Plants useful in the present invention also include, but are not limited to, crops producing edible flowers such as cauliflower (*Brassica oleracea*), artichoke (*Cynara scolvmus*), and safflower (*Carthamus*, e.g. *tinctorius*); fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut, *Arachis hypoaeae*), orange (*Citrus*, e.g. *maxima*), peach (*Prunus*, e.g. *persica*), pear (*Pyra*, e.g. *communis*), pepper (*Solanum*, e.g. *capsicum*), plum (*Prunus*, e.g. *domestica*), strawberry (*Fragaria*, e.g. *moschata*), tomato (*Lycopersicon*, e.g. *esculentum*); leafs, such as alfalfa (*Medicago*, e.g. *sativa*), sugar cane (*Saccharum*), cabbages (such as *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*) yam (*Dioscorea*, e.g. *esculenta*), sweet potato (*Ipomoea batatas*); seeds, such as bean (*Phaseolus*, e.g. *vulgaris*), pea (*Pisum*, e.g. *sativum*), soybean (*Glycine*, e.g. max), wheat (*Triticum*, e.g. *aestivum*), barley (*Hordeum*, e.g. *vulgare*), corn (*Zea*, e.g. *mays*), rice (*Oryza*, e.g. *sativa*); grasses, such as *Miscanthus* grass (*Miscanthus*, e.g., *giganteus*) and switchgrass (*Panicum*, e.g. *virgatum*); trees such as poplar (*Populus*, e.g. *tremula*), pine (*Pinus*); shrubs, such as cotton (e.g., *Gossypium hirsutum*); and tubers, such as kohlrabi (*Brassica*, e.g. *oleraceae*), potato (*Solanum*, e.g. *tuberosum*), and the like.

Plant Transformation

The expression constructs described herein can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isoinerase gene, which provides the ability to metabolize mannose (U.S. Pat. Nos. 5,767,378 and 5,994,629).

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobaclerium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667-674 (1992)) using particle bombardment into cells of type C long-term regenerable callus, and also by Vasil et al. (Biotechnology1 11:1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using Agrobacterium has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

For example, rice (Oryza sativa) can be used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the Agrobacterium tumefaciens strain LBA4404 (Agrobacterium) containing the desired vector construction. Agrobacterium is cultured from glycerol stocks on solid YPC medium (100 mg/L spectinomycin and any other appropriate antibiotic) for about 2 days at 28° C. Agrobacterium is re-suspended in liquid MS-CIM medium. The Agrobacterium culture is diluted to an OD600 of 0.2-0.3 and acetosyringone is added to a final concentration of 200 uM. Acetosyringone is added before mixing the solution with the rice cultures to induce Agrobacterium for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of Agrobacterium. For constructs utilizing the PMI selectable marker gene (Reed et al., In Vitro Cell. Dev. Biol.-Plant 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 umol photons/m$^2$/s) on plates of RMOP medium (Svab, Z., Hajdukiewicz, P. and Maliga, P. (1990) PNAS 87, 8526-8530) containing 500 ug/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346349) is separated on 1% Tris-borate (TBE) agarose gels, transferred to nylon membranes (Amersham) and probed with .sup.32P-labeled random primed DNA sequences corresponding to a 0.7 kb BamHI/HindIII DNA fragment from pC8 containing a portion of the rps 7/12plastid targeting sequence. Homoplasmic shoots are rooted aseptically on spectinomycin-containing MS/IBA medium (McBride, K. E. et al. (1994) PNAS 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified genetic properties.

The following examples are offered by way of illustration and not by way of limitation.

EXPERIMENTAL

Example 1

Monocot and Dicot Optimized Genes

Dicot and monocot plant synthetic genes were designed using the backtranslation program in Vector NTI 9.0. Four protein sequences were backtranslated into monocot optimized and dicot optimized coding sequences using the preferred codons for monocots or dicots. Additional sequence was added to the 5' and 3' end of each cellulase gene coding sequence for cloning and differential targeting to subcellular compartments. These sequences included a BamHI cloning site, Kozak sequence, and N-terminal signal sequence at the 5' end. Vacuolar or ER targeting sequences, and a SacI cloning site was added at the 3' end. Silent mutations were introduced to remove any restriction sites which interfered with cloning strategies. Synthetic genes were synthesized by GENEART (Germany). Table 1 outlines several genes and components of expression cassettes which are described further in the Examples.

TABLE 1

Sequences described in the examples and the sequence listing.

| SEQ ID NO: | Sequence Name | Sequence function |
|---|---|---|
| 2 | BPAO | Vacuole sorting signal peptide |
| 3 | GY1 signal sequence | Glycine max GY1 ER signal sequence |
| 4 | ER retention sequence | |
| 5 | Sporamin targeting sequence | Vacuolar sorting signal peptide |
| 6 | FNR targeting sequence | Plastid targeting sequence |
| 7 | Conglycinin targeting sequence | Protein storage vacuole targeting sequence |
| 8 | Gamma-zein 27 kD signal sequence | ER targeting sequence |
| 9 | Cestrum promoter | Constitutive dicot promoter |
| 10 | Cellobiohydrolase | Dicot optimized CBH1 gene |
| 12 | Cellobiohydrolase | Dicot optimized CBH2 gene |
| 14 | Cellobiohydrolase | Monocot optimized CBH1 gene |
| 16 | Cellobiohydrolase | Monocot optimized CBH2 gene |
| 18 | Cellobiohydrolase | Monocot optimized CBH1 gene |

Example 2

Construction of Plant Expression Vectors

Expression vectors capable of directing the expression of cellulases in transgenic plants were designed for both monocot and dicot optimized cellulases. Tobacco expression vectors used the constitutive promoter Cestrum yellow leaf curl virus (CYLCV) promoter plus leader sequence (SEQ ID NO:9) to drive expression of the dicot optimized cellulase genes. Tobacco expressed cellulases were targeted to the endoplasmic reticulum (ER) via fusion to the *Glycine max* glycinin GY1 signal sequence (SEQ ID NO:3) and the ER retention sequence (SEQ ID NO:4). Tobacco expressed cellulases were targeted to the vacuole via fusion of the cellulase gene with the sporamin vacuolar targeting sequence (SEQ ID NO:5) at the C-terminus (Plant Phys 114: 863-870 (1997)) and the GY1 signal sequence at the N-terminus. Plastid targeting of the cellulase was via the transit peptide (SEQ ID NO:6) from ferredoxin-NADP+ reductase (FNR) of *Cyanophora paradoxa* fused to the N-terminus (FEBS Letters 381: 153-155 (1996)).

The *Glycine max* glycinin GY1 promoter and signal sequence (GenBank Accession X15121) was used to drive soybean seed specific expression of cellulases. Targeting of the cellulase in soybean involved either the C-terminal addition of ER retention sequence (SEQ ID NO:4) or protein storage vacuole (PSV) sequence, (SEQ ID NO:7), from beta-conglycinin (Plant Phys 2004:134, 625-639).

The maize PepC promoter (The Plant Journal 1994: 6(3), 311-319) was used to drive maize leaf specific expression of each monocot optimized cellulase. The cellulase gene was fused to the gamma zein 27 kD signal sequence (SEQ ID NO:8) at the N-terminus to target through the ER and fused to the vacuole sequence domain (VSD) from barley polyamine oxidase (SEQ ID NO:2) to direct the cellulase into the leaf vacuole (Plant Phys 2004: 134, 625-639). Alternatively the ER retention sequence (SEQ ID NO:4) was used in place of the VSD to retain the cellulase in the ER. Plastid targeted constructs contained the FNR transit peptide described above. Each of the maize optimized cellulases was cloned behind the rice glutelin promoter for expression in the endosperm of the maize seed. As described above, additional sequences were added for targeting of the protein to the ER of the endosperm. Vector component information is shown in Table 2. All expression cassettes were subcloned into a binary vector for transformation into tobacco, soybean, and maize using recombinant DNA techniques that are known in the art.

Table 2. Plant Expression Vectors Used for Transgenic Tobacco, Maize, and Soybean Event Production.

| Crop | Enzyme (Enzyme Class) | Promoter | Subcellular Targeting | Construct number |
|---|---|---|---|---|
| tobacco | SEQ ID NO: 10 (CBH1) | Constitutive (CYLCV) | Vacuolar-sporamin (SEQ ID NO: 5) | 15935 |
| tobacco | SEQ ID NO: 10 (CBH1) | Constitutive (CYLCV) | ER (SEQ ID NO: 3 and 4) | 15936 |
| tobacco | SEQ ID NO: 10 (CBH1) | Constitutive (CYLCV) | Plastid | 17024 |
| tobacco | SEQ ID NO: 12 (CBH2) | Constitutive (CYLCV) | ER (SEQ ID NO: 3 and 4) | 17022 |
| tobacco | SEQ ID NO: 12 (CBH2) | Constitutive (CYLCV) | Vacuolar-sporamin (SEQ ID NO: 5) | 17023 |
| tobacco | SEQ ID NO: 12 (CBH2) | Constitutive (CYLCV) | Plastid | 17034 |
| maize | SEQ ID NO: 14 (CBH1) | Leaf (PepC) | Vacuolar-BPAO (SEQ ID NO: 2) | 15942 |
| maize | SEQ ID NO: 14 (CBH1) | Leaf (PepC) | ER | 15944 |
| maize | SEQ ID NO: 14 (CBH1) | Leaf (PepC) | Plastid | 17026 |
| maize | SEQ ID NO: 16 (CBH2) | Leaf (PepC) | ER | 17013 |
| maize | SEQ ID NO: 16 (CBH2) | Leaf (PepC) | Vacuolar-BPAO (SEQ ID NO: 2) | 17014 |
| maize | SEQ ID NO: 16 (CBH2) | Leaf (PepC) | Plastid | 17042 |
| maize | SEQ ID NO: 14 (CBH1) | Seed (rice glutelin) | ER | 15943 |
| maize | SEQ ID NO: 18 (CBH1) | Seed (rice glutelin) | ER | 17021 |
| maize | SEQ ID NO: 16 (CBH2) | Seed (rice glutelin) | ER | 17012 |
| soybean | SEQ ID NO: 10 (CBH1) | Seed (soybean glycinin-1) | PSV | 15928 |
| soybean | SEQ ID NO: 10 (CBH1) | Seed (soybean glycinin) | ER | 15929 |
| soybean | SEQ ID NO: 20 (CBH1) | Seed (soybean glycinin) | PSV | 15973 |

| Crop | Enzyme (Enzyme Class) | Promoter | Subcellular Targeting | Construct number |
|---|---|---|---|---|
| soybean | SEQ ID NO: 20 (CBH1) | Seed (soybean glycinin) | ER | 15983 |
| soybean | SEQ ID NO: 12 (CBH2) | Seed (soybean glycinin) | PSV | 15975 |
| soybean | SEQ ID NO: 12 (CBH2) | Seed (soybean glycinin) | ER | 15982 |

Example 3

Protein Analysis of Transgenic Plants

Protein extracts were obtained from approximately 100 mg of leaf tissue or flour generated from maize and soybean seed from non-transgenic and transgenic plants. Leaf material was placed into 96 deep well blocks containing small steel balls and pre-cooled on dry ice. Samples were ground to a fine powder using a Geno/G rinder (SPEC/CertiPrep, Metuchen, N.J.). Flour samples were prepared by pooling approximately 10-20 seed and grinding to a fine powder using a KLECO Grinder (Gracia Machine Company, Visalia, Calif.). Samples were extracted in 250-500 μl of either Western Extraction Buffer (WEB=12.5 mM sodium borate, pH 10; 2% BME; and 1% SDS) or assay buffer at room temperature for approximately 30 minutes followed by centrifugation for 5 minutes at 13,000 rpm.

SDS-polyacrylamide gel electrophoresis (SDS-PAGE) was performed by transferring 100 μl of WEB samples to an eppendorf tube and add 25 μl 4× BioRad LDS or modified BioRad loading buffer (4× BioRad LDS:BME at a ratio of 2:1). Heat samples for 10 minutes at 70° C. then immediately place on ice for 5 minutes. Spin samples briefly, and transfer back on to ice. Sample extracts (5-10 μl) were run on BioRad 4-12% Bis/Tris protein gel (18 well) using MOPS buffer.

Immunoblot analysis was performed by transferring SDS-PAGE gels onto a nitrocellulose membrane using chilled Nupage transfer buffer (Invitrogen) for 30 minutes at 100 volts. Total protein transferred to the blot was visualized using Ponceau stain (Sigma). Following Ponceau staining, the membrane was incubated in blocking buffer for 30 minutes in TBST wash buffer (30 mM Tris-HCL, pH 7.5, 100 mM NaCl, and 0.05% Tween 20) with 3% dry milk, then washed three times for 5 minutes in TBST. Polyclonal goat or rabbit primary antibody was added at 1 ug/ml in TBST wash buffer with 3% milk, and the blot incubated 2 hours to overnight. Following overnight incubation, the blot was washed three times for 5 minutes each in TBST wash buffer. Secondary antibody (Rabbit-AP or Goat-AP) was diluted 1:8000 (in TBST) and added to blot for 30 minutes. Following incubation in the secondary antibody, the blot was again washed three times for 5 minutes each. Visualization of immuno reactive bands was carried out by adding Moss BCIP/NBT-alkaline phosphatase substrate. Blots were rinsed thoroughly in water following incubation in the BCIP/NBT substrate and allowed to air dry.

Western blots analysis of sample extracts used for activity analysis showed a correlation between accumulation of an immuno-reactive protein and enzyme activity (described in Example 4). CBH1 with ER targeting sequence (construct 15936) was detected as a band that migrates close to the predicted size of the full length enzyme (56.6 kD with the ER targeting sequence and retention sequence and 53.3 when the ER targeting sequence is processed off to form the CBH1 enzyme in the ER). A second, smaller band of about 51 kD was also detected in the western blot. CBH1 targeted to the leaf vacuole (construct 15935) accumulated predominately as a 51 kD protein.

Western blot analysis was used to screen transgenic maize plants generated with construct 15942 and construct 15944. The maize leaf expressed CBH1 (SEQ ID NO: 14) with ER targeting sequence (construct 15944) was detected as a band that migrates close to the predicted size of the full length enzyme (57 kD). A second, broad band centered around 51 kD was also detected. Vacuolar targeted CBH1 (SEQ ID NO: 14) (construct 15942) shows a broad band at approximately 51 kD with a minor band at 57 kD.

The level of CBH1 targeted to the ER or to the vacuole of maize leaf was also measured after 24 days of leaf growth (ER-targeted) and 41 days of leaf growth (vacuole-targeted).

Leaves were also harvested 60 days after planting of maize expressed CBH1 targeted to the ER and allowed to dry. Fifty milligrams of dry leaf powder was extracted in a strong denaturing buffer and samples analyzed by SDS-PAGE and Western Blot as described above.

Example 4

Enzyme Extraction and Activity Analysis of Transgenic Events

Approximately 100 mg of fresh leaf tissue or seed flour of a transgenic plant was extracted in 5 to 10 ml of one of the following buffers: (A) 100 mM Na acetate, 0.02% Tween, 0.02% Na azide pH 4.75, 1% PVP and Complete protease inhibitor cocktail tablets (Roche); (B) 100 mM Na acetate, 1 mg/ml BSA, 0.02% Tween, and 0.02% Na azide pH 4.75; or (C) 100 mM Sodium Acetate pH 5.3, 100 mM NaCl, 1 mg/ml Gelatin, 1 mM EDTA, 0.02% Tween-20, 0.02% NaN$_3$ Alternative buffers for extracting protein from leaf or from seed are well known in the art. Samples were placed on benchtop rotators for 30-60 minutes then centrifuged at 3000 rpm for 10 minutes. For fresh leaf samples, the amount of total protein extracted was measured by Pierce BCA protocol as outlined in product literature. Cellulase activity assays were carried out using one of the following substrates: pNP-lactoside, methylumbelliferyl-lactoside (MUL), carboxymethyl-cellulose, oat-μ glucan, phosphoric acid treated cellulose (PASC), Avicel, or other commercially available substrates used for measuring cellulase activity following previously published protocols (Methods in Enzymology, Vol 160). Enzyme activity data generated for transgenic plants expressing CBH1 is outlined in Tables 3-7. Enzyme activity data generated for maize leaf expressing CBH2 in the ER and in the vacuole is shown in Table 8. Enzyme activity data generated for maize leaf expression of CBH1 in the ER of 24-day old and in the vacuole of 41-day old green leaves, as well as in the ER of 100-day old dry leaves was generated.

In summary, the tobacco transgenic plants indicate that targeting cellulases to the vacuole with the sporamin vacuole targeting sequence facilitates the accumulation of more protein in tobacco leaves than targeting the same protein to the ER. In addition, targeting the cellulases to the vacuole with the sporamin vacuole targeting sequence does not lead to the high level of enzyme accumulation as observed in maize plants expressing the same cellulase targeted to the vacuole with the BPAO targeting sequence.

The transgenic maize data is consistent with the transgenic tobacco data in that targeting to the vacuole leads to a higher accumulation of cellulases than observed when the same enzyme is targeted to the ER. However, targeting the cellulase enzyme to the ER results in the accumulation of protein products that are closer to the predicted size of the cellulase than is observed when the same cellulase is targeted to the vacuole. This analysis was performed by Western blot and by comparing the products produced by transgenic plants expressing either vacuole or ER targeted cellulases.

It is noted that higher molecular weight enzymes accumulate in ER targeted versions of the expression constructs. These higher molecular weight products are more likely to be full length products of the gene. The higher molecular weight products may be truncated versions of the gene that are processed by, for example, glycosylation, which may modify the size of the products observed by Western blot. Lastly, these higher molecular weight products may be full length products of the gene in addition to being further processed by, for example, glycosylation, which may modify the size of the products observed by Western blot.

TABLE 3

Summary of cellobiohydrolase I (CBHI) activity in transgenic tobacco events expressing dicot optimized CBH1 (SEQ ID NO: 10) targeted to the vacuole (construct 15935) and ER (construct 15936) of tobacco leaves. Samples were extracted in buffer A and CBH1 activity was assayed on methylumbelliferyl-lactoside as the substrate.

| Construct number | Plant ID number | nmol/min/mg protein | Western blot | Avicel binding assay |
|---|---|---|---|---|
| 15935 | Nt22-1A | 0.466 | + | ND |
| 15935 | Nt22-6B | 0.519 | + | ND |
| 15935 | Nt22-7A | 0.685 | + | ND |
| 15935 | Nt22-10A | 0.587 | + | ND |
| 15935 | Nt22-11A | 0.500 | + | ND |
| 15935 | Nt22-15A | 0.363 | + | ND |
| 15935 | Nt22-16A | 1.337 | + | + |
| 15935 | Nt22-17A | 0.650 | + | ND |
| 15935 | Nt22-18A | 1.079 | + | ND |
| 15935 | Nt22-19A | 0.009 | − | − |
| 15935 | Nt22-23B | 1.811 | + | + |
| 15935 | Nt22-24B | 1.151 | + | ND |
| 15935 | Nt22-30B | 1.338 | + | ND |
| 15936 | Nt23-2B | 0.170 | + | ND |
| 15936 | Nt23-5A | 0.118 | + | ND |
| 15936 | Nt23-9A | 0.670 | + | ND |
| 15936 | Nt23-11A | 0.666 | + | + |
| 15936 | Nt23-12A | 0.410 | + | ND |
| 15936 | Nt23-16A | 0.354 | + | ND |
| 15936 | Nt23-17B | 0.597 | + | ND |
| 15936 | Nt23-22A | 0.484 | + | ND |
| 15936 | Nt23-23B | 0.907 | + | + |
| 15936 | Nt23-24B | 0.162 | + | ND |
| 15936 | Nt23-26B | 0.203 | + | ND |
| 15936 | Nt23-29B | 0.626 | + | ND |
| 15936 | Nt23-30B | 0.082 | − | − |
| 15936 | Nt23-32B | 0.190 | + | ND |
| Non-transgenic control | Non-transgenic control | 0.007 | − | ND |
| Non-transgenic control | Non-transgenic control | −0.010 | − | ND |

ND = not determined

TABLE 4

Summary of cellobiohydrolase I (CBHI) activity in transgenic maize events (construct 15942) expressing monocot optimized CBH1 encoded by the polynucleotide of SEQ ID NO: 14, targeted to the vacuole of maize leaves. Samples were extracted in buffer A and CBH1 activity was assayed on methylumbelliferyl-lactoside as the substrate.

| Plant ID Number | Avg nmol/min/mg Protein | Standard Deviation | Western Blot |
|---|---|---|---|
| 001A | 1.51 | 0.46 | + |
| 002A | 0.63 | 0.05 | + |
| 003A | 0.53 | 0.18 | + |
| 004A | 1.01 | 0.34 | + |
| 005A | 0.04 | 0.01 | − |
| 006A | 0.03 | 0.01 | − |
| 007A | 2.34 | 0.48 | + |
| 008A | 0.48 | 0.05 | + |
| 009A | 0.65 | 0.05 | + |
| 011A | 0.11 | 0.05 | − |
| 012A | 1.47 | 0.12 | + |
| 013A | 1.88 | 0.62 | + |
| 014A | 0.68 | 0.14 | + |
| 015A | 3.45 | 0.17 | + |
| 016A | 3.17 | 0.42 | + |
| 018A | 2.32 | 0.52 | + |
| 019A | 4.33 | 2.02 | + |
| 021A | 0.88 | 0.01 | + |
| 022A | 2.69 | 0.15 | + |
| 023A | 0.03 | 0.00 | − |
| 024A | 4.84 | 0.36 | + |
| 025A | 1.77 | 0.22 | + |
| 026A | 0.57 | 0.04 | + |
| 027A | 1.87 | 0.77 | + |
| 028A | 8.43 | 1.09 | + |
| 029A | 1.88 | 0.70 | + |
| 030A | 1.08 | 0.04 | + |
| Nontransgenic control | 0.07 | 0.00 | − |

TABLE 5

Summary of cellobiohydrolase I (CBHI) activity in transgenic maize events (construct 15944) expressing monocot optimized CBH1 encoded by the polynucleotide of SEQ ID NO: 14, targeted to the ER of maize leaves. Samples were extracted in buffer A and CBH1 activity was assayed on methylumbelliferyl-lactoside as the substrate.

| Plant ID Number | Avg nmol/min/mg protein | Standard Deviation | Western Blot |
|---|---|---|---|
| 001A | 1.71 | 0.09 | + |
| 002A | 0.01 | 0.00 | − |
| 003A | 1.10 | 0.13 | + |

TABLE 5-continued

Summary of cellobiohydrolase I (CBHI) activity in transgenic maize events (construct 15944) expressing monocot optimized CBH1 encoded by the polynucleotide of SEQ ID NO: 14, targeted to the ER of maize leaves. Samples were extracted in buffer A and CBH1 activity was assayed on methylumbelliferyl-lactoside as the substrate.

| Plant ID Number | Avg nmol/min/mg protein | Standard Deviation | Western Blot |
|---|---|---|---|
| 004A | 0.03 | 0.00 | − |
| 005A | 0.63 | 0.04 | + |
| 006A | ND | ND | − |
| 007A | ND | ND | − |
| 008A | ND | ND | − |
| 009A | 1.20 | 0.04 | + |
| 010A | ND | ND | − |
| 011A | ND | ND | + |
| 012A | 1.34 | 0.09 | + |
| 013A | 5.85 | 0.43 | + |
| 014A | 1.20 | 0.07 | + |
| 015A | 1.95 | 0.19 | + |
| 016A | ND | ND | − |
| 017A | 2.50 | 0.07 | + |
| 018A | ND | ND | + |
| 019A | ND | ND | − |
| 020A | 0.91 | 0.07 | + |
| 021A | 2.34 | 0.05 | + |
| 022A | ND | ND | − |
| 023A | ND | ND | + |
| 024A | ND | ND | − |
| 025A | ND | ND | + |
| 026A | ND | ND | + |
| 027A | 1.51 | 0.09 | + |
| 028A | ND | ND | + |
| 029A | ND | ND | + |
| 030A | ND | ND | + |
| 031A | 2.36 | 0.07 | + |
| 032A | ND | ND | − |
| 033A | 1.59 | 0.11 | + |
| 034A | ND | ND | + |
| 035A | 1.14 | 0.11 | + |
| 036A | 1.06 | 0.09 | + |
| 037A | 1.27 | 0.21 | + |
| 038A | 0.55 | 0.01 | + |
| 039A | 1.51 | 0.02 | + |
| 040A | 1.36 | 0.15 | + |
| 041A | 0.53 | 0.01 | + |
| 042A | 0.02 | 0.00 | − |
| 043A | 1.15 | 0.05 | + |
| 044A | 0.81 | 0.03 | + |
| 045A | ND | ND | − |
| 046A | 0.52 | 0.03 | + |

ND = not determined

Example 5

Crystalline Cellulose Binding and Hydrolysis Assays

Avicel Binding Assay: Approximately 100 mg of leaf tissue was extracted in 5 mL of assay buffer (A), as described above. Following extraction, approximately 250 ul of sample was incubated with 25 mg Avicel (crystalline cellulose) for 0 and 60 minutes. Zero time point samples were added to eppendorf tubes placed on ice prior to addition of extracts and immediately processed. Samples were incubated for 60 minutes on a benchtop vortex at room temperature. After incubation, samples were centrifuged for 5 minutes at 13000 rpm in an eppendorf centrifuge. Supernatants were carefully removed and the Avicel washed 3× with ice cold water. Following the final wash, 80 ul of western extraction buffer (WEB) and 25 ul of BioRad 4× loading buffer was added the sample. Samples were vortexed then placed at 70 degrees for 10 minutes. The Avicel was pelleted at 13000 rpm and the supernatants removed and analyzed by western blot as described above.

Transgenic plants derived from construct 15935 (Nt22-16A, Nt22-19A) and construct 15936 (Nt23-11A, Nt23-23B, Nt23-30B) were analyzed through the Avicel Binding assay described in the above paragraph. Plants Nt22-16A, Nt23-11A and Nt23-23B were positive by western blot analysis while plants Nt22-19A and Nt23-30B were negative in the Avicel Binding assay. This data is summarized in table 3.

Avicel Hydrolysis assay. Transgenic leaf samples were lyophilized then ground to a find powder using a Kleco grinder. Approximately 150 mg of ground leaf material was weighed out and extracted in 4 ml of buffer A at RT for 30 minutes. Samples were centrifuged and supernatants removed. One ml of each leaf extract, fungal expressed BD22308 or *Trichoderma reesei* CBH1 (Megazyme International) enzyme, or fungal enzymes added to non-expressing transgenic extract was added to 50 mg of Avicel and samples placed on a vortex at 37 degrees. Protein concentrations were measured using BCA reagent (Pierce). Duplicate 100 µl samples were removed at 0, 24, 48, and 72 hours. Sugar analysis was carried out by HPLC analysis. Data generated for maize transgenic plants transformed with construct 15944 (CBH1 (SEQ ID NO: 14)) targeted to the ER) is shown in table 6.

Protein extracts from the transgenic plants were equivalent for total protein content; however, the data does not represent the relative level of expression of CBH1 (SEQ ID NO: 14)) in transgenic plants. The data in table 6 demonstrates that plant expressed cellulases are active in the Avicel assay which demonstrates binding of the cellulase to a substrate and subsequent cellulase activity.

TABLE 6

Liberation of cellobiose from Avicel using cellulases expressed by transgenic maize plants.

| Transgenic number | mg/mL cellobiose produced at 72 hours | Standard Deviation |
|---|---|---|
| 013A | 2.644 | 0.264 |
| 017A | 1.549 | 0.366 |
| 036A | 1.631 | 0.710 |
| 042A (negative control) | −0.086 | 0.001 |
| 042A + CBH1 (SEQ ID NO: 11) fungal enzyme (0.09 mg/ml) | 0.317 | 0.087 |
| 042A + Mega Tr. (0.25 mg/ml) | 3.226 | 0.083 |
| CBH1 (SEQ ID NO: 11) fungal enzyme (0.09 mg/ml) | 1.565 | 0.734 |
| Megazyme TrCBH1 fungal enzyme (0.05 mg/ml) | 3.719 | 0.831 |
| Buffer only | 0 | 0 |

Mega Tr. = commercially available CBH1, Megazyme TrCBH1

Example 6

CBH1 Protein in Plant Leaf Tissue

Transgenic corn plants containing the CBH1 expression constructs described in Example 2 were generated. The transgenic corn plants were grown in a greenhouse and leaf tissue harvested at various points during the development of the plant. The greenhouse grown plants were allowed to senese by harvesting ears and withdrawing water at approximately 45 to 110 days after planting. The stover tissue resulting from senescence was analyzed for cellulase protein. Harvested stover tissue was stored at −20 degrees C. before analysis and just prior to analysis was lyophilized for 18 to 24 hours. Lyophilized stover tissue was subsequently pulverized to a fine powder using a Kleco Grinder (Gracia Machine Company, Visalia, Calif.) to produce stover flour. Cellulase activity in the stover flour was detected essentially as described in Examples 3 and 4 using approximately 100 mg of stover flour. Table 7 outlines the detection of cellulase enzymes in plant tissue at a representative time point during the growth, development and senescence of the plant. Cellulase activity measured as a function of grams of tissue indicates that cellulases are stable and active in stover tissue derived from transgenic corn plants.

Transgenic corn 019A transformed with construct 15942 (vacuole targeted CBH1) was crossed with a different corn variety to create an F1 hybrid seed. F1 hybrid seed was grown in the greenhouse and tissue samples were collected from stover flour essentially as described above in Example 6. Collected samples were analyzed for cellulase activity essentially as described in Examples 3 and 4. Cellulase activity data generated for the F1 hybrid plants is outlined in Table 7.

Transgenic corn 017A transformed with construct 15944 (ER targeted CBH1) was allowed to self pollinate and set T1 seed. T1 seed was grown in the greenhouse and tissue samples were collected from stover flour essentially as described above in Example 6. Collected samples were analyzed for cellulase activity essentially as described in Examples 3 and 4. Cellulase activity data generated for the T1 transgenic plants is outlined in Table 7.

Stover collected from transgenic maize plants was allowed to sit at room temperature for 1 year prior to assaying for cellulase activity essentially as described in Example 3. After 1 year at room temperature, the cellulase activity in the stover remained comparable to that observed at the time the stover was harvested. These observations suggest the cellulases remain stable in stover tissue.

TABLE 7

Transgenic corn plants expressing CBH1 targeted to the vacuole or targeted to the ER. Plants were assayed using MUL as the substrate.

| Enzyme (SEQ ID NO) | Targeting sequence (SEQ ID NO) | Event name | Western blot | Activity assay (SD)* of green tissue collected at 55 days after planting | Activity assay (SD)* of stover flour | Fold change from green to stover |
|---|---|---|---|---|---|---|
| CBH1 (11) | Vacuole (2) | F1 22 | Negative | −460 (189) | −138 (15) | ND |
| CBH1 (11) | Vacuole (2) | F1 25 | Positive | 3164 (252) | 11238 (593) | 3.6 |
| CBH1 (11) | Vacuole (2) | F1 27 | Positive | 3445 (132) | 10225 (156) | 3.0 |
| CBH1 (11) | Vacuole (2) | F1 28 | Positive | 3102 (145) | 12296 (695) | 4.0 |
| CBH1 (11) | Vacuole (2) | F1 31 | Positive | 3288 (171) | 16044 (428) | 4.9 |
| CBH1 (11) | Vacuole (2) | F1 33 | Positive | 3482 (131) | 13144 (266) | 3.8 |
| CBH1 (11) | Vacuole (2) | F1 34 | Positive | 3604 (65) | 14378 (156) | 4.0 |
| CBH1 (11) | Vacuole (2) | F1 36 | Positive | 2813 (242) | 10985 (54) | 3.9 |
| CBH1 (11) | Vacuole (2) | F1 37 | Positive | 3365 (122) | 13137 (555) | 3.9 |
| CBH1 (11) | ER (4) | 017A-21 | Positive | 898 (16) | 979 (29) | 1.1 |
| CBH1 (11) | ER (4) | 017A-22 | Positive | 1686 (36) | 3719 (72) | 2.2 |
| CBH1 (11) | ER (4) | 017A-40 | Positive | 1037 (19) | 1833 (61) | 1.8 |
| CBH1 (11) | ER (4) | 017A-24 | Positive | 2342 (98) | 5738 (56) | 2.5 |
| CBH1 (11) | ER (4) | 017A-27 | Positive | 494 (17) | 787 (445) | 1.6 |
| CBH1 (11) | ER (4) | 017A-32 | Positive | 213 (34) | 17 (106) | 0.1 |
| CBH1 (11) | ER (4) | 017A-33 | Positive | 1113 (33) | 1100 (131) | 1.0 |
| CBH1 (11) | ER (4) | 017A-35 | Positive | 835 (56) | 1069 (77) | 1.3 |
| CBH1 (11) | ER (4) | 017A-36 | Positive | 1140 (58) | −58 (125) | ND |
| CBH1 (11) | ER (4) | 017A-39 | Positive | 763 (92) | 81 (4) | 0.1 |

*activity measured as average nmol/min/g of tissue

Example 7

CBH2 Protein in Plant Tissue

Transgenic corn plants containing the CBH2 (SEQ ID NO: 16) expression constructs described in Example 2 were generated. The T0 transgenic corn plants were self pollinated to generate T1 seed and plants. The greenhouse grown plants were allowed to senese by harvesting ears and withdrawing water at approximately 45-110 days after planting. The stover tissue resulting from senescence was analyzed for cellulase protein. Harvested stover tissue was stored at −20 degrees C. before analysis and just prior to analysis was lyophilized for 18 to 24 hours. Lyophilized stover tissue was subsequently pulverized to a fine powder using a Kleco Grinder (Gracia Machine Company, Visalia, Calif.) to produce stover flour. Cellulase activity in the stover flour was determined essentially as described in Examples 3 and 4 using approximately 100 mg of stover flour. Table 8 outlines the detection of cellulase enzymes in T1 transgenic plant tissue at a representative time point during the growth, development and senescence of the plant.

TABLE 8

T1 transgenic corn plants expressing CBH2 (SEQ ID NO: 12). Enzyme activity was measured using PASC as the substrate.

| Enzyme (SEQ ID NO) | Targeting sequence (SEQ ID NO) | Event name | Western blot | Activity assay (SD)* of green tissue collected at 55 days after planting | Activity assay (SD)* of stover flour | Fold change from green to stover |
|---|---|---|---|---|---|---|
| CBH2 (12) | Vacuole (2) | 003A-31 | Positive | 764 (20) | 5408 (432) | 7.0 |
| CBH2 (12) | Vacuole (2) | 003A-32 | Negative | −89 (84) | −89 (52) | ND |
| CBH2 (12) | Vacuole (2) | 003A-35 | Positive | 663 (79) | 5495 (189) | 8.3 |
| CBH2 (12) | Vacuole (2) | 003A-37 | Positive | 776 (164) | 7188 (247) | 9.2 |
| CBH2 (12) | Vacuole (2) | 003A-39 | Positive | 620 (176) | 6434 (249) | 10.4 |
| CBH2 (12) | Vacuole (2) | 003A-40 | Positive | 615 (154) | 6032 (323) | 9.8 |
| CBH2 (12) | Vacuole (2) | 020A-23 | Positive | 846 (58) | 7762 (173) | 9.2 |
| CBH2 (12) | Vacuole (2) | 020A-24 | Positive | 697 (56) | 5215 (274) | 7.5 |
| CBH2 (12) | Vacuole (2) | 020A-25 | Negative | 132 (58) | 123 (38) | 0.9 |
| CBH2 (12) | Vacuole (2) | 020A-26 | Positive | 569 (151) | 4862 (113) | 8.5 |
| CBH2 (12) | Vacuole (2) | 020A-27 | Positive | 864 (48) | 7059 (217) | 8.2 |
| None | None | Non-transgenic control | Negative | 0.3 (48) | 136 (373) | ND |

*activity measured as average nmol/min/gram of tissue

Example 8

Transgenic Maize Plants Expressing Endoglucanse

An endoglucanase isolated from a fungal species will be identified and cloned into expression vectors containing the PEPC green tissue promoter or into expression vectors containing the rice glutelin promoter for seed expression. The expression cassettes will be subcloned into transformation vectors containing the selectable marker PMI. Transgenic maize plants will be generated by agrobacterium transformation and subsequent selection for PMI expression. Transgenic maize plants will be confirmed by Taqman analysis of any component within the expression cassette containing the endoglucanase or the PMI selectable marker.

Transgenic maize plants will be assayed for endoglucanase expression essentially as described in Example 3. Target tissues will be leaves, seed and stover.

Example 9

Transgenic Sugarcane Expressing Cellulases

The binary vector transformation constructs for maize described in Example 2 and Table 2 will be used to generate transgenic sugarcane plants. A fragment of the binary vector containing the cellulase expression cassette and the selectable marker expression cassette will be isolated using standard molecular biology techniques. This fragment will be used to transform sugarcane callus using biolistic transformation technology known to one of skill in the art. Transgenic sugarcane plants will be generated from the callus and selected based upon Taqman analysis for any component of the cellulase expression cassette or the selectable marker expression cassette.

Transgenic sugarcane plants will be evaluated for expression of cellulases essentially as described in Example 3. The tissues to be evaluated include stems, leaves, stover and juice.

Example 10

Transgenic Cellulase Expression in the Seed

Transgenic soybean plants were generated using the transformation vectors 15928 and 15929 which are described in Example 2. The expression constructs used in these experiments used a seed preferred promoter to drive expression of a CBH1 (SEQ ID NO: 10) cellulase targeted to either the vacuole (construct 15928) or the ER (15929). Seeds from the transgenic plants were harvested and assayed essentially as described in Example 3 for CBH1 activity. In addition to enzyme activity, plants were evaluated by Western blot to determine the sizes of the CBH1 protein that were produced. CBH1 activity data is summarized in Tables 9 and 10. Similar data generated will be generated for CBH2 (constructs 15975 and 15982 from Example 2).

Soybean seed expressed CBH1 with vacuole targeting sequence (construct 15928) was detected as 2 bands running at approximately 58 kD and 53 kD. The predicted size of the vacuole targeted protein is 53.7. ER targeted CBH1 (construct 15929) showed a predominant single band at approximately 60 kD. The predicted size of the ER targeted CBH1 protein is 53.3 kD. This observation is consistent with the data generated in transgenic maize.

TABLE 9

Transgenic seeds from soybean expressing CBH1 (SEQ ID NO: 10) targeted to the vacuole (SEQ ID NO: 2).

| Construct | Sample | Avg nmol/min/mg TSP | STDev | Avg nmol/min/g flour | STDev | Western Results |
|---|---|---|---|---|---|---|
| 15928 | 008A | 0.45 | 0.28 | 46.06 | 1.93 | positive (weak) |
| 15928 | 010A | 0.89 | 0.03 | 61.45 | 2.42 | positive (weak) |
| 15928 | 012A | 10.50 | 0.59 | 822.55 | 0.48 | positive |
| 15928 | 609A018A | 3.78 | 0.19 | 274.94 | 17.40 | positive |
| 15928 | 609A024A | 8.82 | 0.37 | 680.62 | 11.37 | positive |
| 15928 | 609A032A | 0.15 | 0.01 | 11.91 | 0.70 | n.d. |
| 15928 | 609A033A | 0.36 | 0.00 | 23.32 | 0.39 | n.d. |
| 15928 | 609A044A | 0.19 | 0.01 | 12.99 | 0.58 | n.d. |
| 15928 | 0651A004A | 6.53 | 0.40 | 480.53 | 5.40 | positive |
| 15928 | 0897A016B | 6.48 | 0.17 | 482.67 | 2.51 | positive |
| 15928 | S0901A003A | 5.17 | 0.11 | 431.95 | 8.51 | positive |
| 15928 | 0901A006A | 4.58 | 0.08 | 375.44 | 4.23 | positive |
| 15928 | 0901A007B | 3.29 | 0.04 | 284.48 | 0.85 | positive |
| WT | Non-Transgenic | 0.01 | 0.04 | 0.96 | 3.42 | negative |

TABLE 10

Transgenic seeds from soybean expressing CBH1 (SEQ ID NO: 10) targeted to and retained in the ER (SEQ ID NO: 3 and 4)

| Construct | Sample | Avg nmol/min/mg TSP | STDev | Avg nmol/min/g flour | STDev | Western Results |
|---|---|---|---|---|---|---|
| 15929 | A032A | 7.231 | 0.331 | 563.432 | 20.193 | positive |
| 15929 | A001A | 5.703 | 0.533 | 413.917 | 11.730 | positive |
| 15929 | A035A | 0.313 | 0.014 | 22.642 | 1.876 | n.d. |
| 15929 | A043A | 0.135 | 0.012 | 10.836 | 1.225 | n.d. |
| 15929 | A052A | 7.656 | 0.087 | 571.564 | 9.903 | positive |
| 15929 | A037A | 1.334 | 0.024 | 109.815 | 1.313 | positive |
| 15929 | A001A | 2.127 | 0.051 | 165.048 | 3.324 | positive |
| 15929 | A001C | 2.202 | 0.103 | 165.552 | 7.056 | positive |
| 15929 | A010A | 2.446 | 0.034 | 178.694 | 3.502 | positive |
| 15929 | A014A | 1.485 | 0.078 | 122.037 | 2.822 | positive |
| 15929 | A015A | 3.877 | 0.025 | 312.550 | 2.105 | positive |
| WT | Non-Transgenic | −0.028 | 0.096 | −2.161 | 7.045 | negative |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a protein storage vacuole targeting sequence operably linked to a nucleic acid encoding a cellobiohydrolase (CBH), which is operatively linked to a plant green tissue specific promoter, wherein the protein storage vacuole targeting sequence comprises the amino acid sequence of SEQ ID NO: 2 or SEQ ID NO:5.

2. The isolated nucleic acid of claim 1, wherein the cellobiohydrolase (CBH) is a protein secreted by a fungus.

3. The isolated nucleic acid of claim 2, wherein the cellobiohydrolase is selected from the group consisting of cellobiohydrolase 1 (CBH1) and cellobiohydrolase 2 (CBH2).

4. The isolated nucleic acid of claim 3, wherein the CBH1 comprises a polypeptide selected from the group consisting of the amino acid sequences of SEQ ID NOs: 11, 15, 19 and 21.

5. The isolated nucleic acid of claim 3, wherein the CBH2 comprises a polypeptide selected from the group consisting of the amino acid sequences of SEQ ID NOs: 13 and 17.

6. A method for accumulating a cellobiohydrolase (CBH) in a transgenic plant comprising the steps of:
    a) operatively linking a plant green tissue specific promoter, a protein storage vacuole targeting sequence and a nucleic acid encoding the cellobiohydrolase, wherein the protein storage vacuole targeting sequence comprises the amino acid sequence of SEQ ID NO: 2 or SEQ ID NO:5; and
    b) generating a transgenic plant wherein the cellobiohydrolase is targeted to the vacuole.

7. The method of claim 6, wherein the cellobiohydrolase is a protein secreted by a fungus.

8. The method of claim 7, wherein the cellobiohydrolase is selected from the group consisting of cellobiohydrolase 1 (CBH1) and cellobiohydrolase 2 (CBH2).

9. The method of claim 8, wherein the CBH1 comprises a polypeptide selected from the group consisting of the amino acid sequences of SEQ ID NOs: 11, 15, 19 and 21.

10. The method of claim 8, wherein the CBH2 comprises a polypeptide selected from the group consisting of the amino acid sequences of SEQ ID NOs: 13 and 17.

11. A transgenic plant cell comprising a nucleic acid molecule comprising a polynucleotide encoding a protein storage vacuole targeting sequence operably linked to a nucleic acid encoding a cellobiohydrolase which is operatively linked to a plant green tissue specific promoter, wherein the protein storage vacuole targeting sequence comprises the amino acid sequence of SEQ ID NO:2 or SEQ ID NO:5.

12. The transgenic plant cell of claim 11, wherein the plant is a monocot.

13. The transgenic plant cell of claim 11, wherein the plant is a dicot.

14. The transgenic plant cell of claim 11, wherein the cellobiohydrolase is a protein secreted by a fungus.

15. The transgenic plant cell of claim 12, wherein the monocot is maize.

16. The transgenic plant cell of claim 14, wherein the cellobiohydrolase is selected from the group consisting of cellobiohydrolase 1 (CBH1) and cellobiohydrolase 2 (CBH2).

17. The transgenic plant cell of claim 16, wherein the CBH1 comprises a polypeptide selected from the group consisting of the amino acid sequences of SEQ ID NOs: 11, 15, 19 and 21.

18. The transgenic plant cell of claim 16, wherein the CBH2 comprises a polypeptide selected from the group consisting of the amino acid sequences of SEQ ID NOs: 13 and 17.

19. A method for accumulating a cellobiohydrolase (CBH) in plant stover comprising the steps of;

a) introducing into a plant cell a nucleic acid construct comprising a polynucleotide encoding a protein storage vacuole sorting signal sequence and a plant green tissue specific promoter, each of which is operably linked to a nucleotide sequence encoding a cellobiohydrolase, wherein the protein storage vacuole sorting signal sequence comprises the amino acid sequence of SEQ ID NO:2 or SEQ ID NO:5;

b) regenerating a transformed plant from said plant cell; and c) allowing the transformed plant to senesce to form stover, thereby accumulating the cellobiohydrolase in said plant stover.

20. The method of claim 19, wherein the heterologous polypeptide accumulates at least 3 fold more cellobiohydrolase in the stover than in the green tissue, wherein the cellobiohydrolase is measured as an amount of cellobiohydrolase per unit of gram of tissue.

21. The method of claim 19, wherein the stover is maize.

22. The method of claim 19, wherein the cellobiohydrolase is a protein secreted by a fungus.

23. The method of claim 19, wherein the cellobiohydrolase is selected from the group consisting of CBH1 and CBH2.

24. The method of claim 23, wherein the CBH1 comprises a polypeptide selected from the group consisting of the amino acid sequence of SEQ ID NOs: 11, 15, 19 and 21.

25. The method of claim 23, wherein the CBH2 comprises a polypeptide selected from the group consisting of the amino acid sequences of SEQ ID NOs: 13 and 17.

26. The method of any one of claims 19 to 21, 22, and 23 to 25, wherein the polypeptide is stable in senesced tissue for at least 2 to 3 months, at least 3 to 6 months, at least 6 to 9 months, at least 9 months to 1 year or more than 1 year.

* * * * *